US010273278B2

(12) United States Patent
Ku et al.

(10) Patent No.: US 10,273,278 B2
(45) Date of Patent: Apr. 30, 2019

(54) EPITOPE RECOGNIZED BY ANTI-INTERFERON GAMMA AUTOANTIBODIES IN PATIENTS WITH DISSEMINATED MYCOBACTERIAL INFECTIONS AND THE APPLICATION THEREFOR

(71) Applicant: CHANG GUNG UNIVERSITY, Tao-Yuan (TW)

(72) Inventors: Cheng-Lun Ku, Tao-Yuan (TW); Chia-Hao Lin, Tao-Yuan (TW); Chih-Yu Chi, Tao-Yuan (TW); Han-Po Shih, Tao-Yuan (TW); Jing-Ya Ding, Tao-Yuan (TW)

(73) Assignee: CHANG GUNG UNIVERSITY, Tao-Yuan (TW)

( * ) Notice: Subject to any disclaimer, the term of this patent is extended or adjusted under 35 U.S.C. 154(b) by 0 days.

(21) Appl. No.: 15/185,172

(22) Filed: Jun. 17, 2016

(65) Prior Publication Data

US 2017/0114112 A1 Apr. 27, 2017

(30) Foreign Application Priority Data

Jun. 18, 2015 (TW) .............................. 104119897 A

(51) Int. Cl.
| | | |
|---|---|---|
| *G01N 33/50* | (2006.01) | |
| *G01N 33/564* | (2006.01) | |
| *G01N 33/68* | (2006.01) | |
| *C07K 14/57* | (2006.01) | |
| *G01N 33/569* | (2006.01) | |
| *A61K 38/00* | (2006.01) | |

(52) U.S. Cl.
CPC ......... *C07K 14/57* (2013.01); *G01N 33/5023* (2013.01); *G01N 33/5055* (2013.01); *G01N 33/564* (2013.01); *G01N 33/5695* (2013.01); *G01N 33/6866* (2013.01); *G01N 33/6869* (2013.01); *A61K 38/00* (2013.01); *G01N 2333/5434* (2013.01); *G01N 2333/57* (2013.01); *G01N 2800/52* (2013.01)

(58) Field of Classification Search
CPC . C07K 14/57; G01N 33/6866; G01N 33/6869
See application file for complete search history.

(56) References Cited

U.S. PATENT DOCUMENTS 6,120,762 A * 9/2000 Johnson ................. C07K 14/57
424/85.5

OTHER PUBLICATIONS

Patel et al., (J Immunol. 2005;175:4769-4776). (Year: 2005).*
Lin et al., Nat.Med . . . , vol. 22, No. 9, pp. 994-1003, (Year: 2016).*
Daniel Lundell, Charles Lunn, David Dalgarno, James Fossetta, Robert Greenberg, Richard Reim, Michael Grace, Satwant Narula, "The carboxyl-terminal region of human interferon gamma is important for biological activity: mutagenic and NMR analysis", Protein Engineering, 1991, pp. 335-341, vol. 4, No. 3, Oxford University Press, UK.
Cheng-Lun Ku, "Molecular Mechanisms of Anti-Interferon Gamma Autoantibodies in Nontuberculous Mycobacterial Infected Patients", Executive Yuan National Science Council Project-Research Project-Results Report, Nov. 5, 2012, Taiwan.
Smita Y. Patel, Li Ding, Margaret R. Brown, Larry Lantz, Ted Gay, Stuart Cohen, Lenna A. Martyak, Bernard Kubak, Steven M. Holland, "Anti-IFN-gamma Autoantibodies in Disseminated Nontuberculous Mycobacterial Infections", The Journal of Immunology, 2005, pp. 4769-4776, vol. 175, The American Association of Immunologists, Inc., USA.

* cited by examiner

*Primary Examiner* — Daniel E Kolker
*Assistant Examiner* — Jegatheesan Seharaseyon
(74) *Attorney, Agent, or Firm* — Cheng-Ju Chiang

(57) ABSTRACT

The present invention discloses a fragment of peptide which can be utilized in patients suffering from a disseminated mycobacterial infection. The fragment of peptide contains a sequence of amino acids with seven residues as formula (I) shown below, wherein $X_1$ is Leucine (Leu); $X_2$ is Proline (Pro); $X_3$ is Glutamate (Glu); $X_4$ is serine (Ser); $X_5$ is Serine (Ser); $X_6$ is Leucine (Leu) and $X_7$ is Arginine (Arg): $X_1$-$X_2$-$X_3$-$X_4$-$X_5$-$X_6$-$X_7$ (I).

5 Claims, 39 Drawing Sheets

Specification includes a Sequence Listing.

Peptide1  QDPYVKEAENLKKYFNAGHSDVADNGTLFL
(SEQ ID NO: 2)

Peptide2  DNGTLFLGILKNWKEESDRKIMQSQIVSFY
(SEQ ID NO: 3)

Peptide3  SQIVSFYFKLFKNFKDDQSIQKSVETIKED
(SEQ ID NO: 4)

Peptide4  VETIKEDMNVKFFNSNKKKRDDFEKLTNYS
(SEQ ID NO: 5)

Peptide5  FEKLTNYSVTDLNVQRKAIHELIQVMAELS
(SEQ ID NO: 6)

Peptide6  IQVMAELSPAAKTGKRKRSQMLFRGRRASQ
(SEQ ID NO: 7)

Fig. 1a

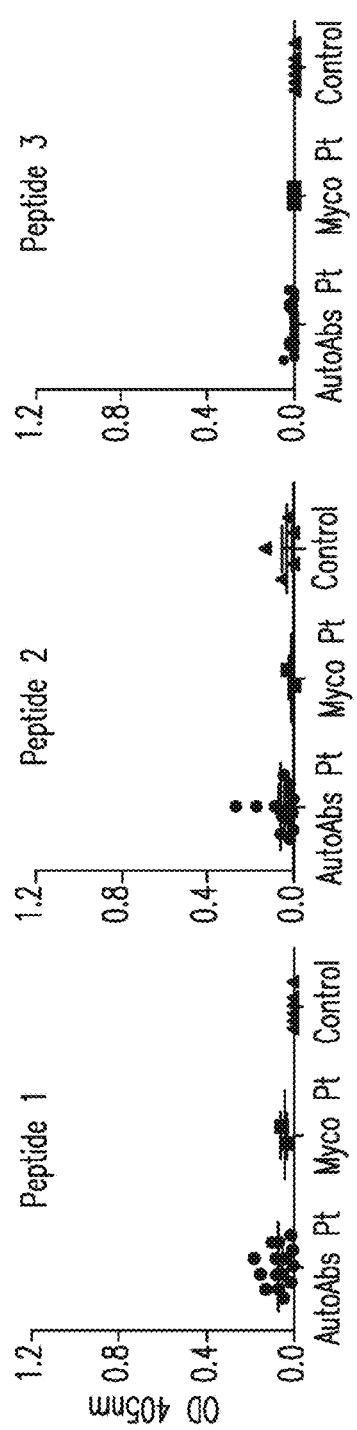
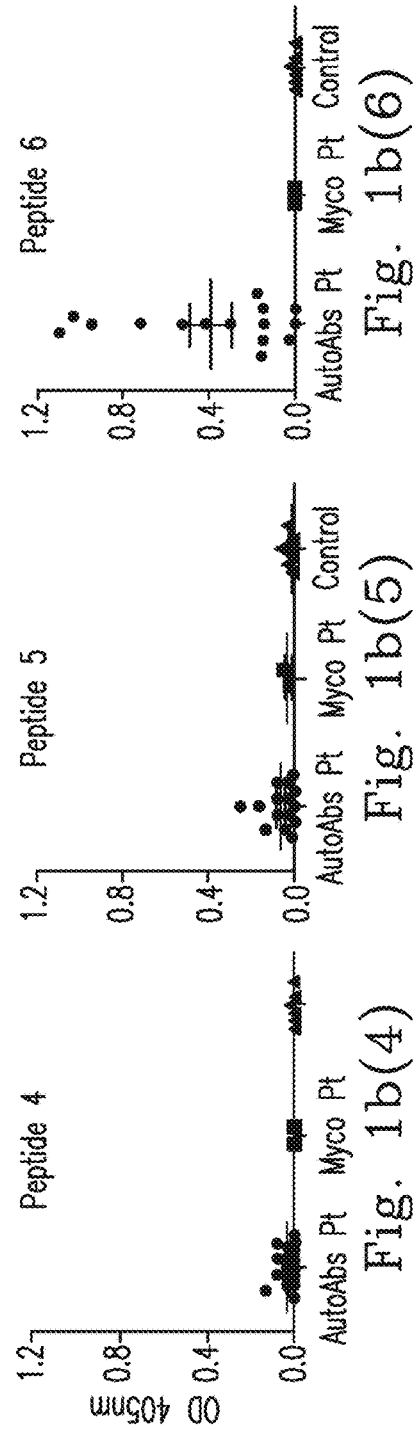

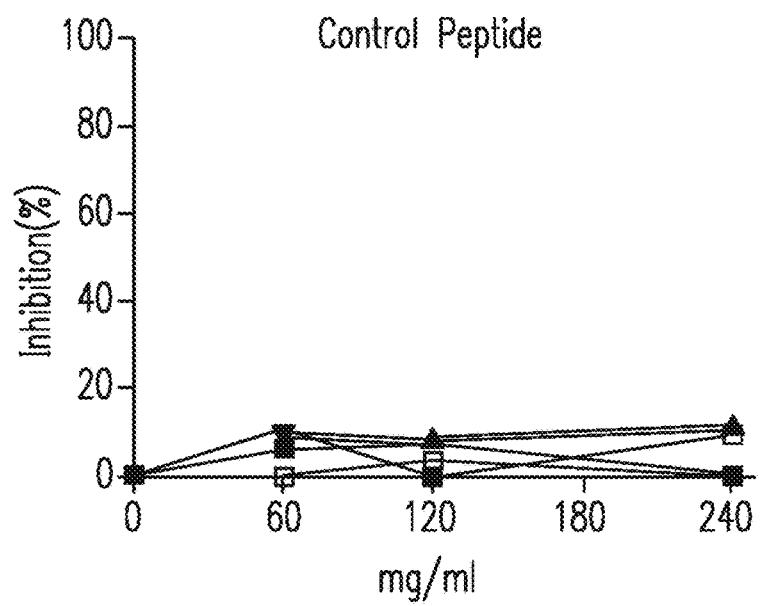
Fig. 1c(1)
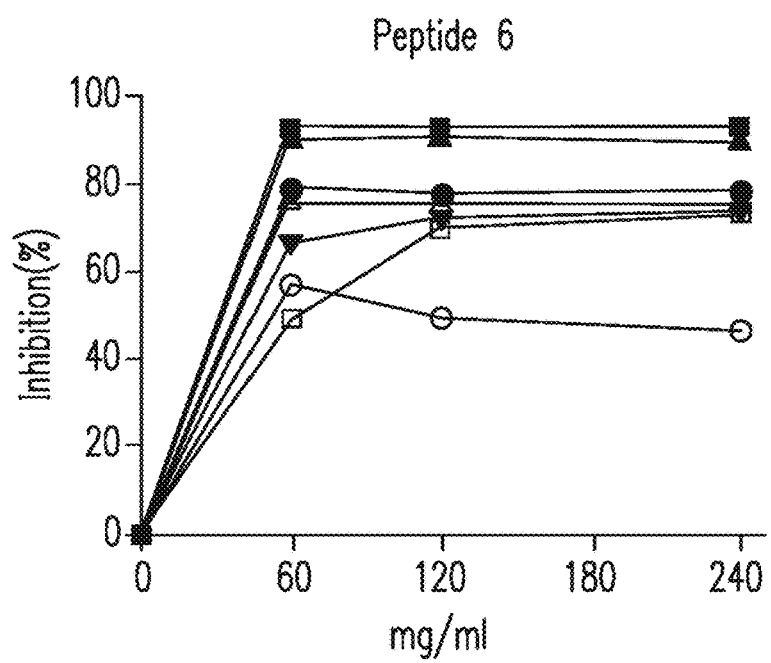
Fig. 1c(2)

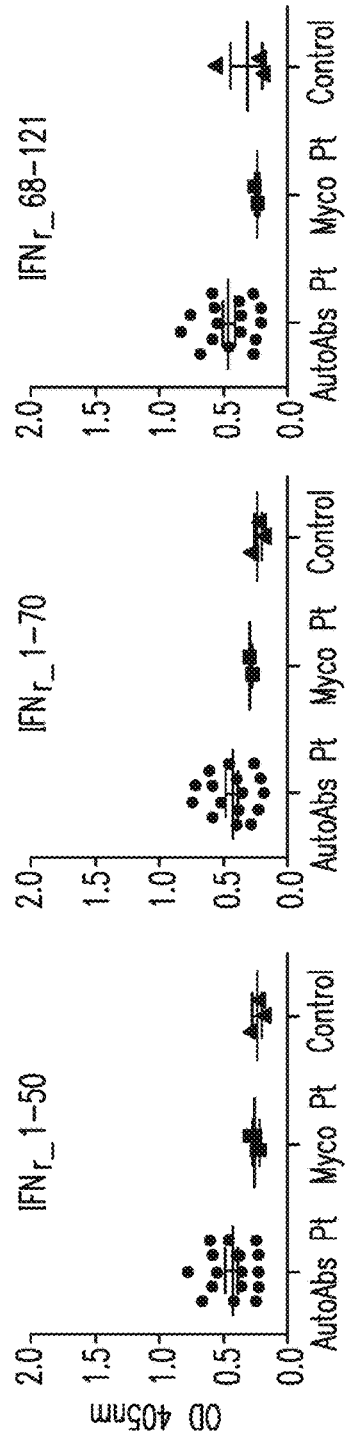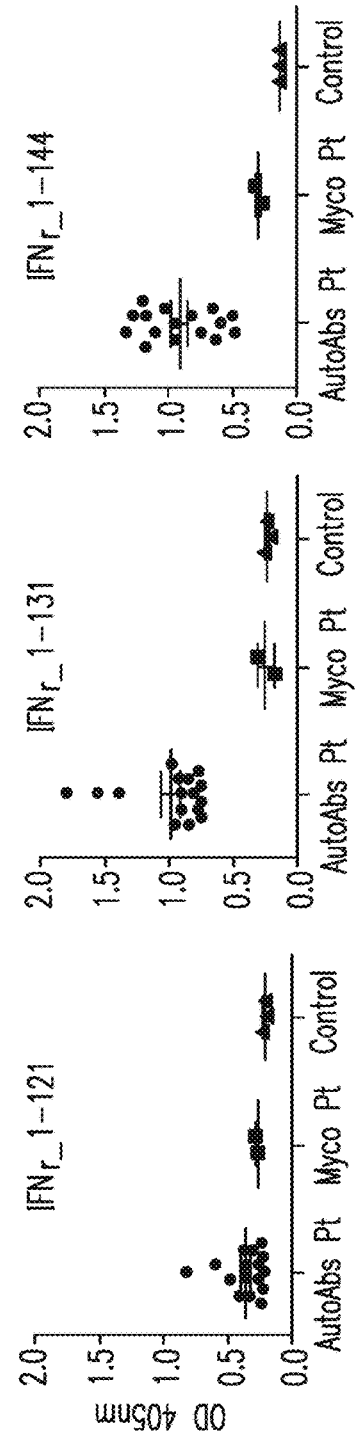
Fig. 1g(1) IFNr_1-50
Fig. 1g(2) IFNr_1-70
Fig. 1g(3) IFNr_68-121
Fig. 1g(4) IFNr_1-121
Fig. 1g(5) IFNr_1-131
Fig. 1g(6) IFNr_1-144

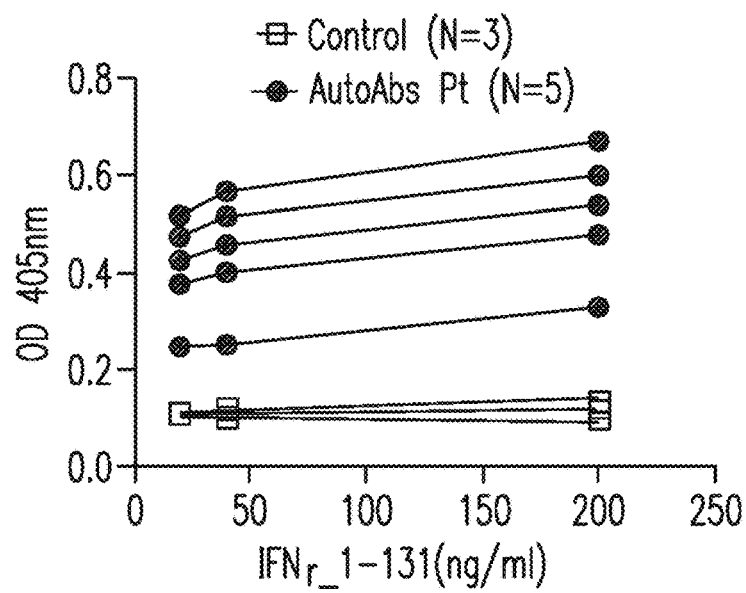
Fig. 2a(1)
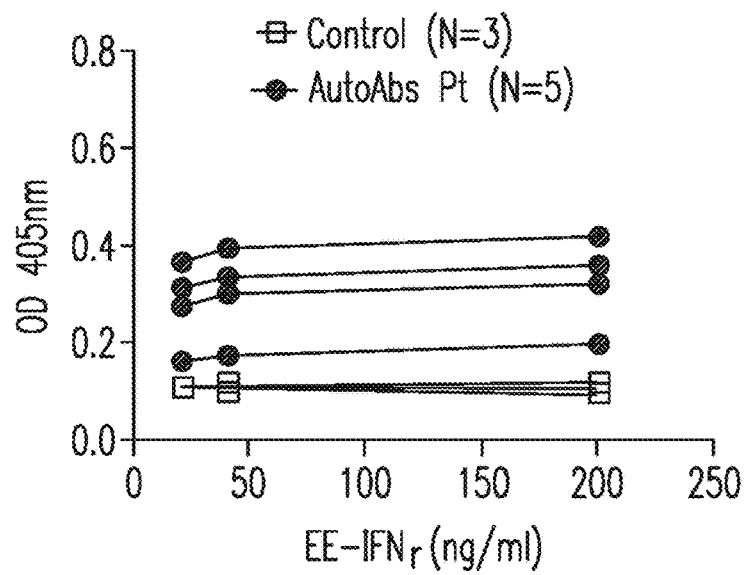
Fig. 2a(2)

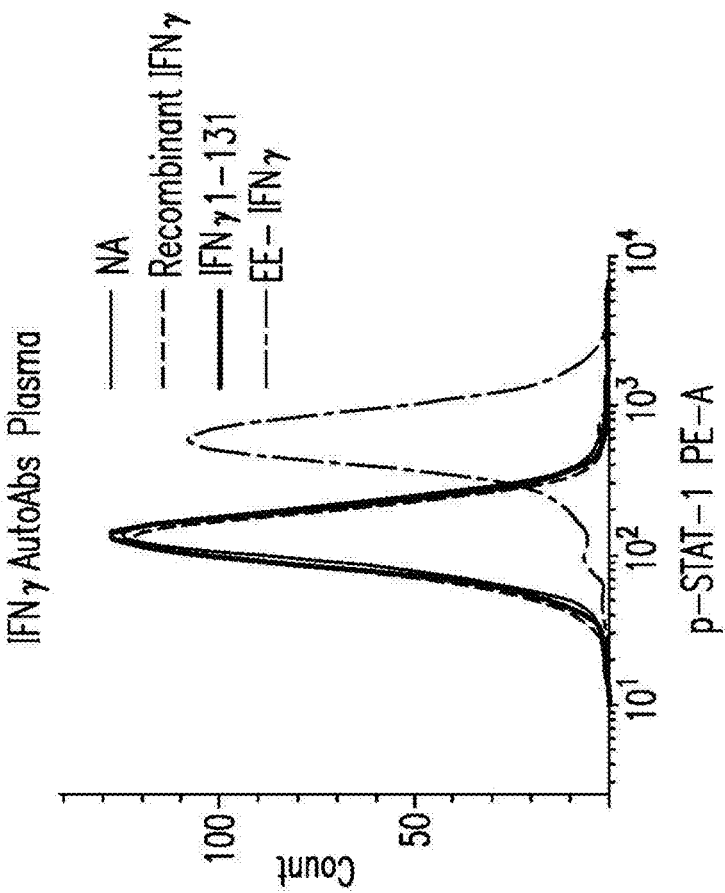
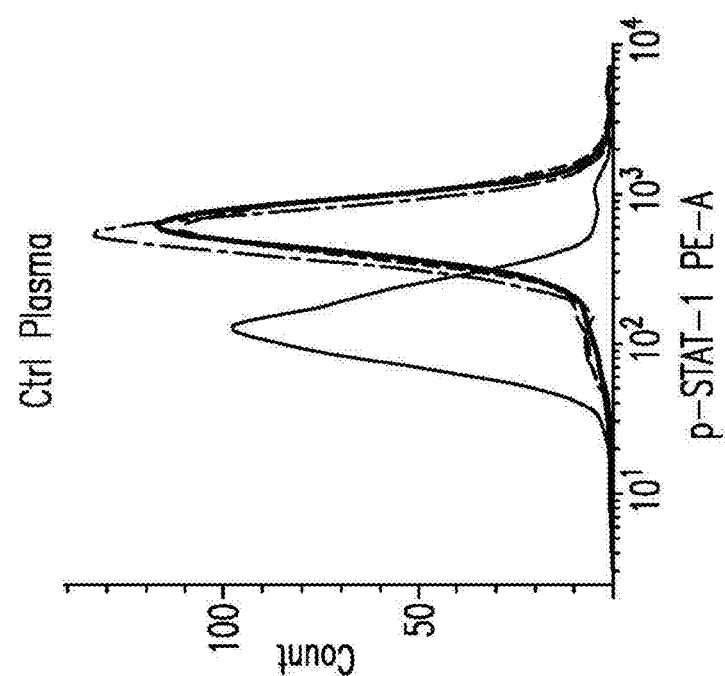
Fig. 2c(2)
Fig. 2c(1)

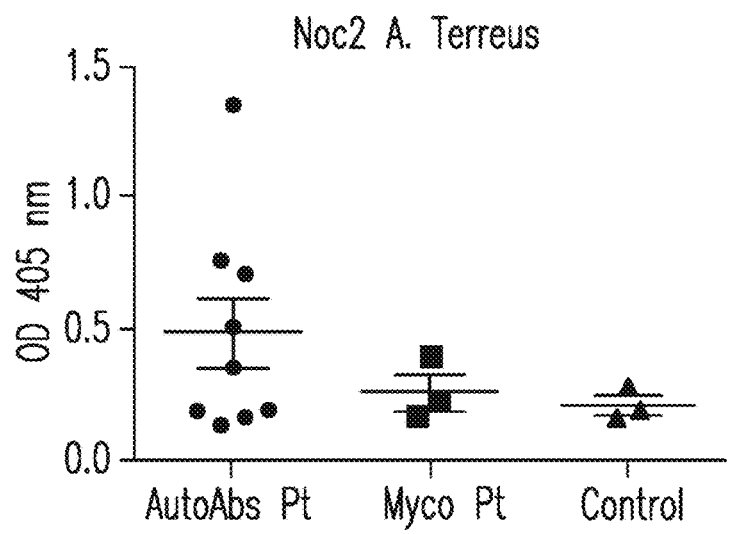
Fig. 3a(1)
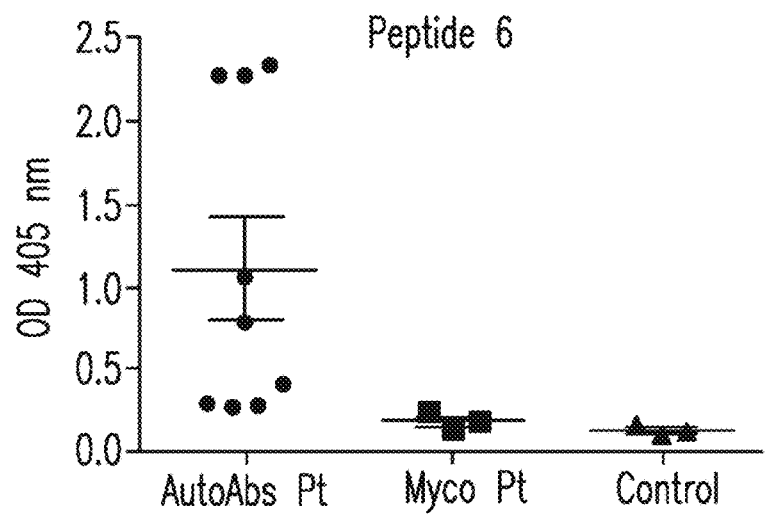
Fig. 3a(2)

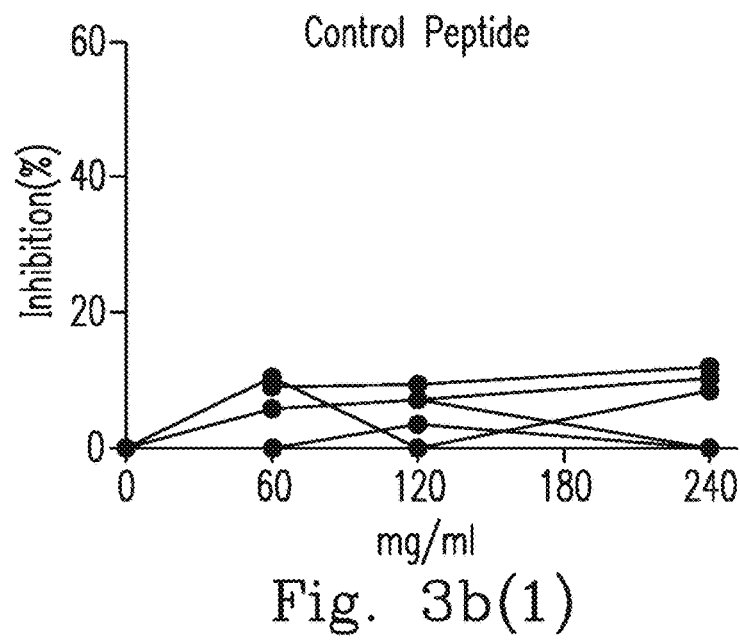
Fig. 3b(1)
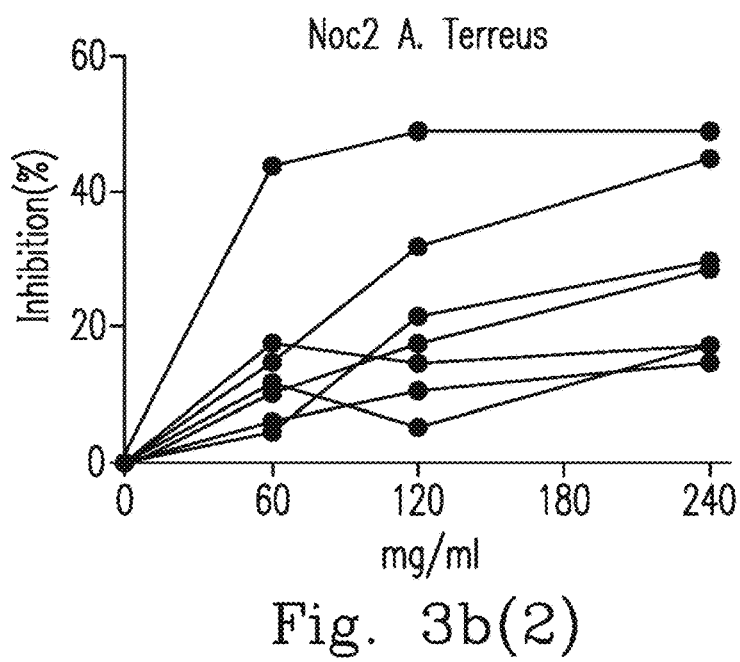
Fig. 3b(2)

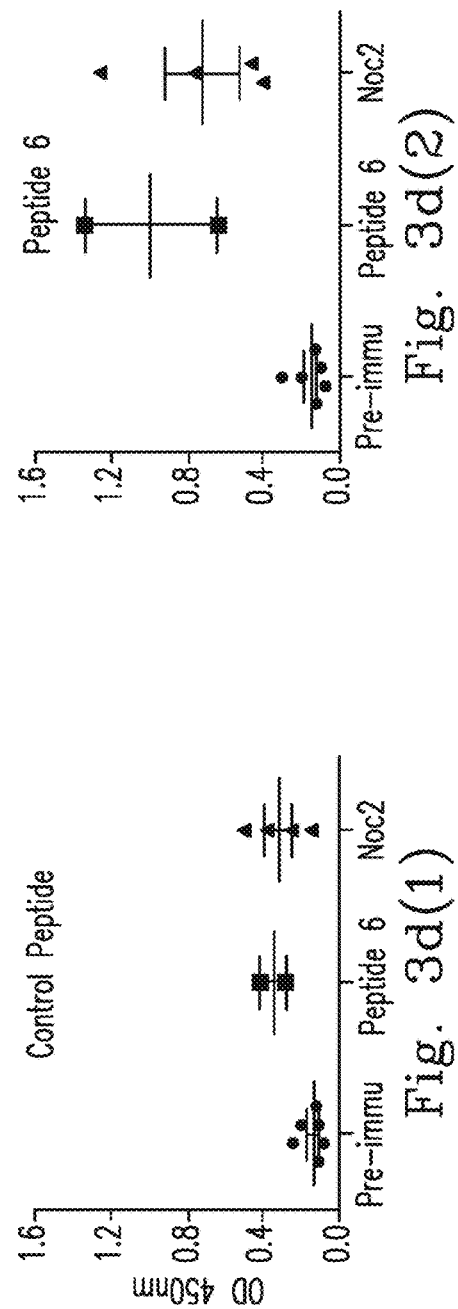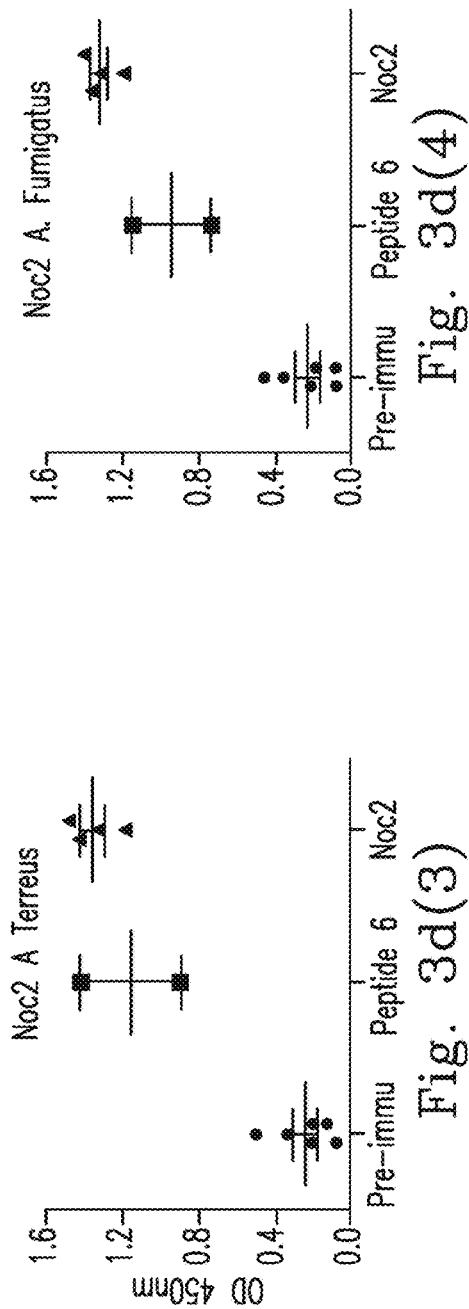

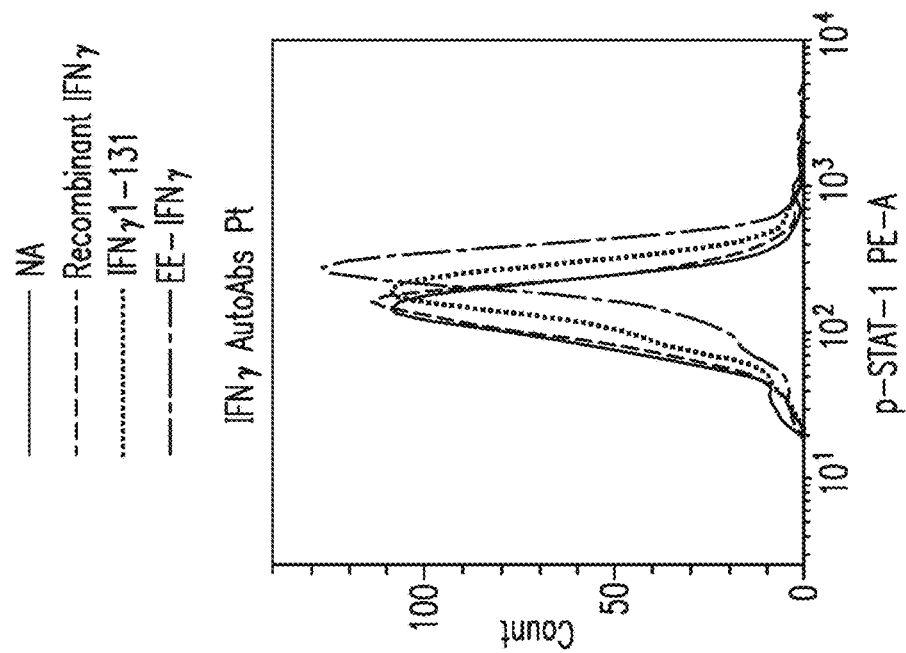
Fig. 4a(2)
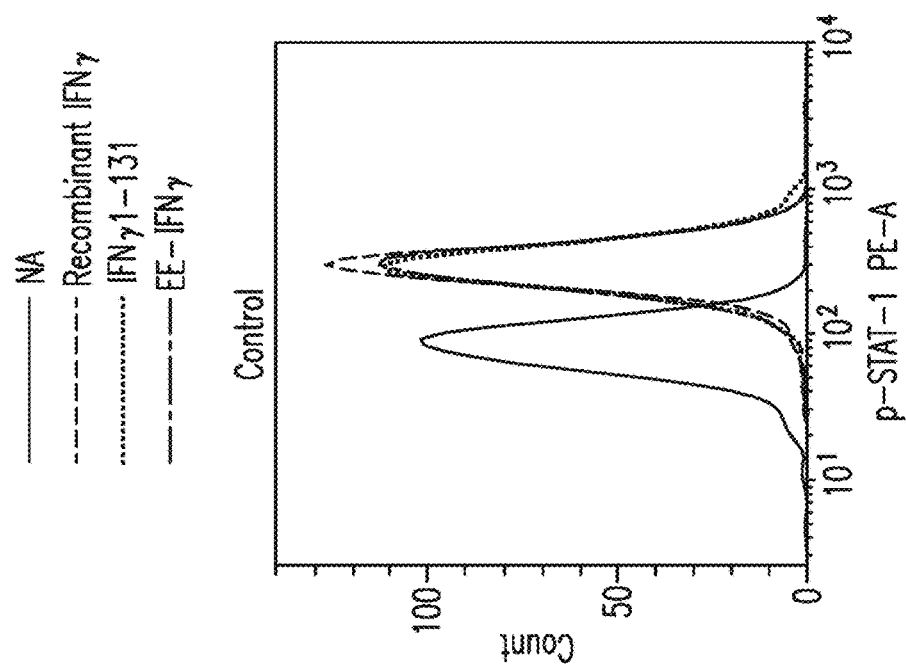
Fig. 4a(1)

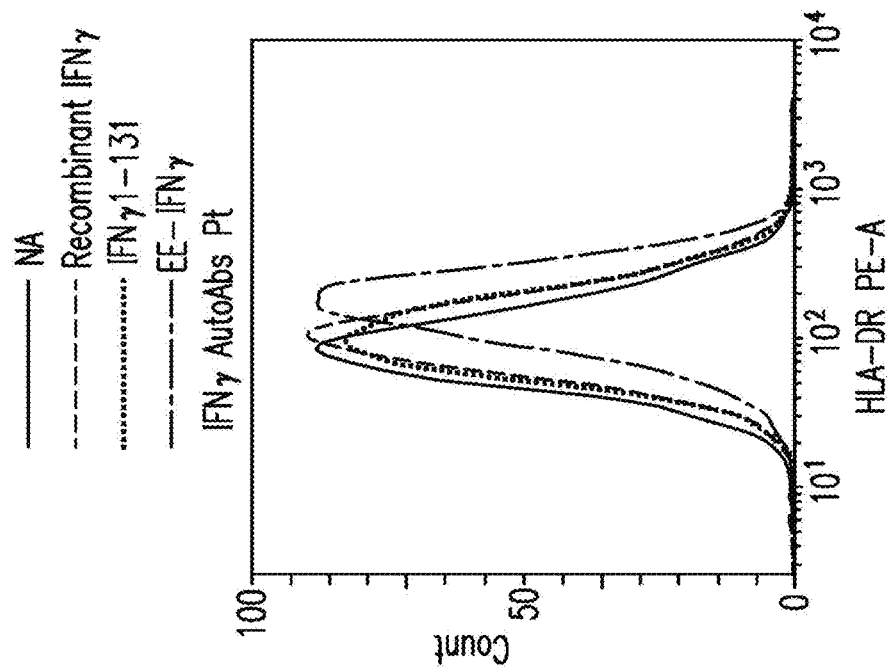
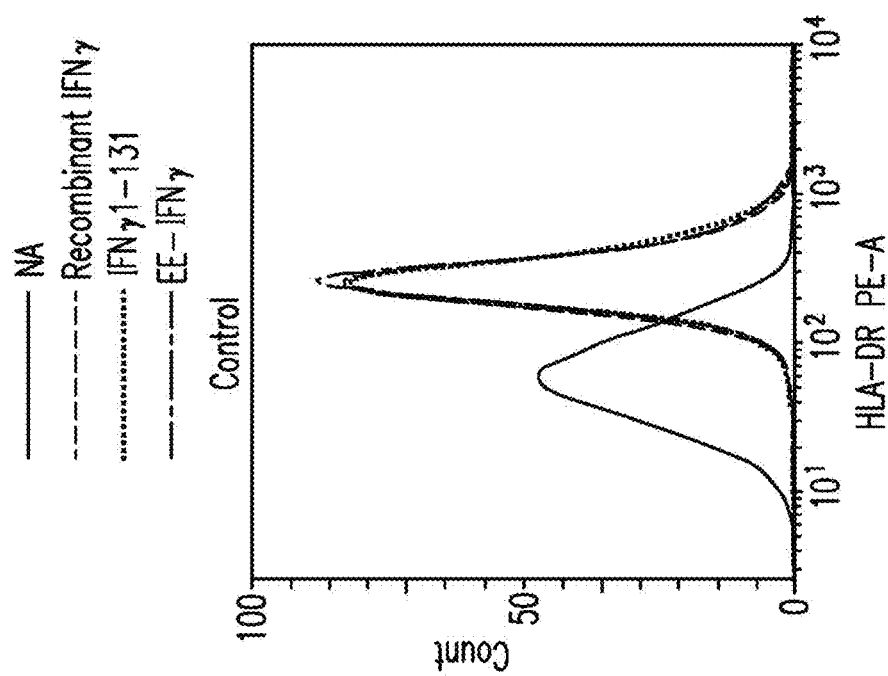
Fig. 4d(2)
Fig. 4d(1)

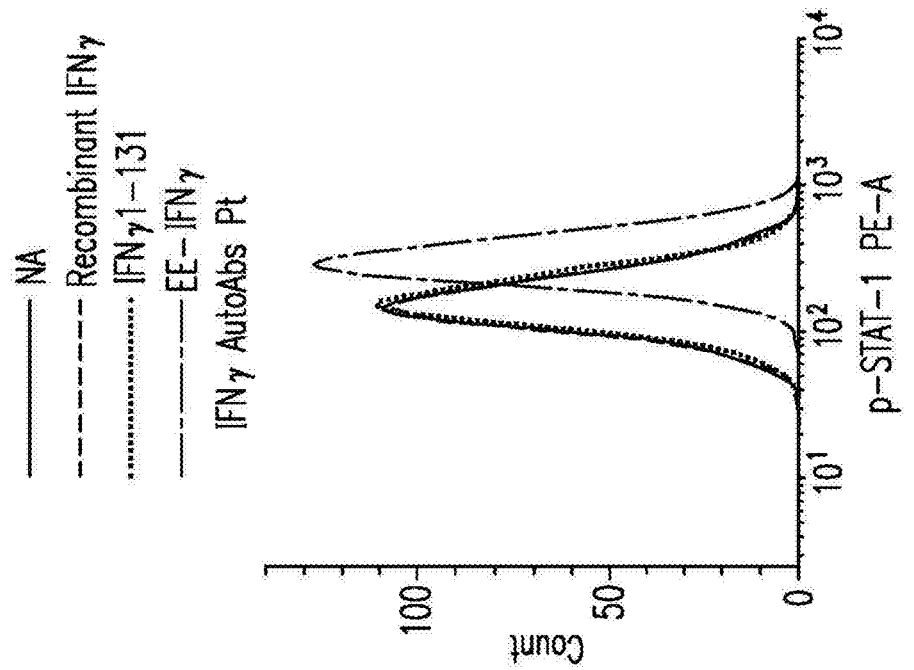
Fig. 4f(2)
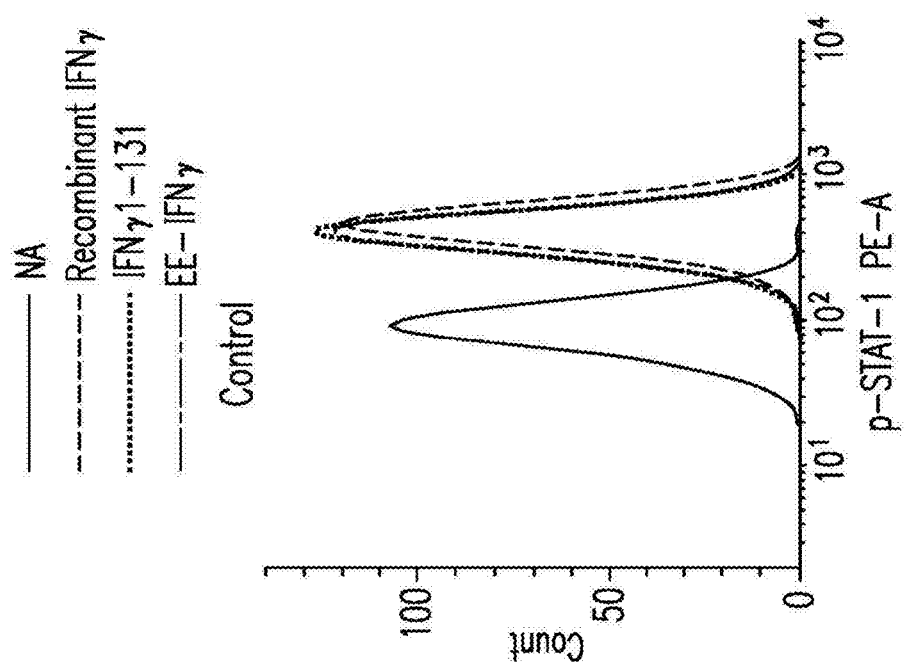
Fig. 4f(1)

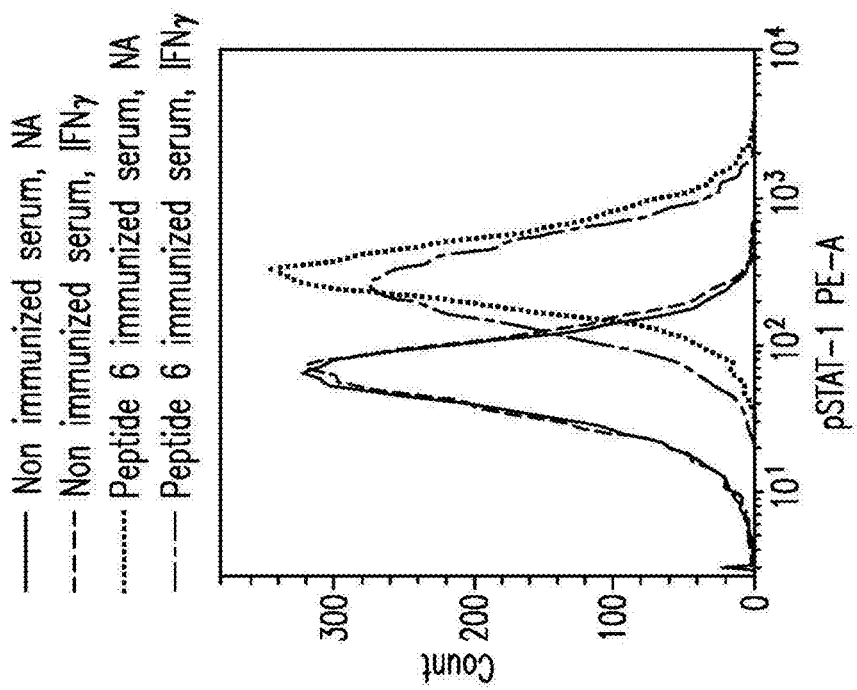
Fig. 13a(2)
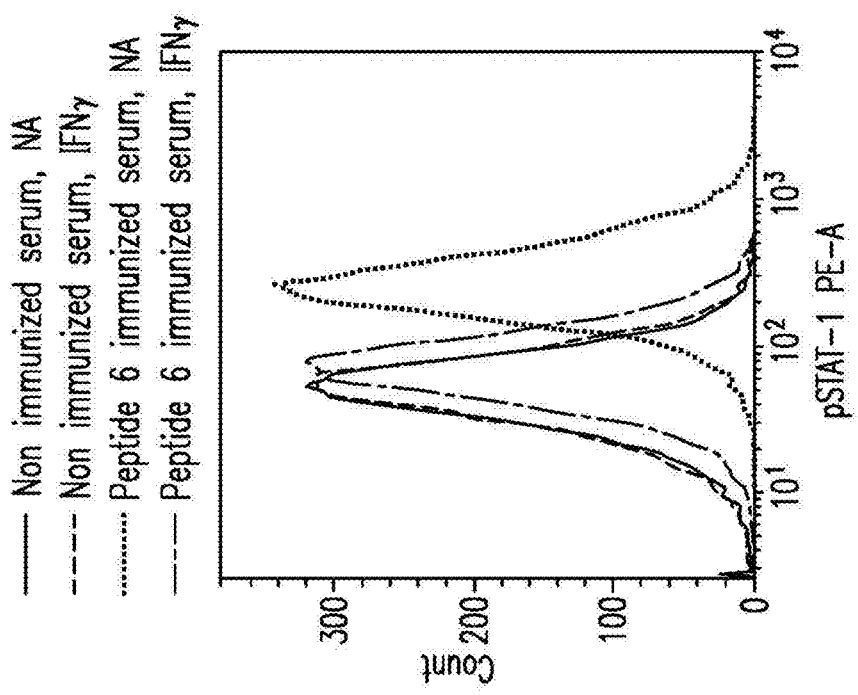
Fig. 13a(1)

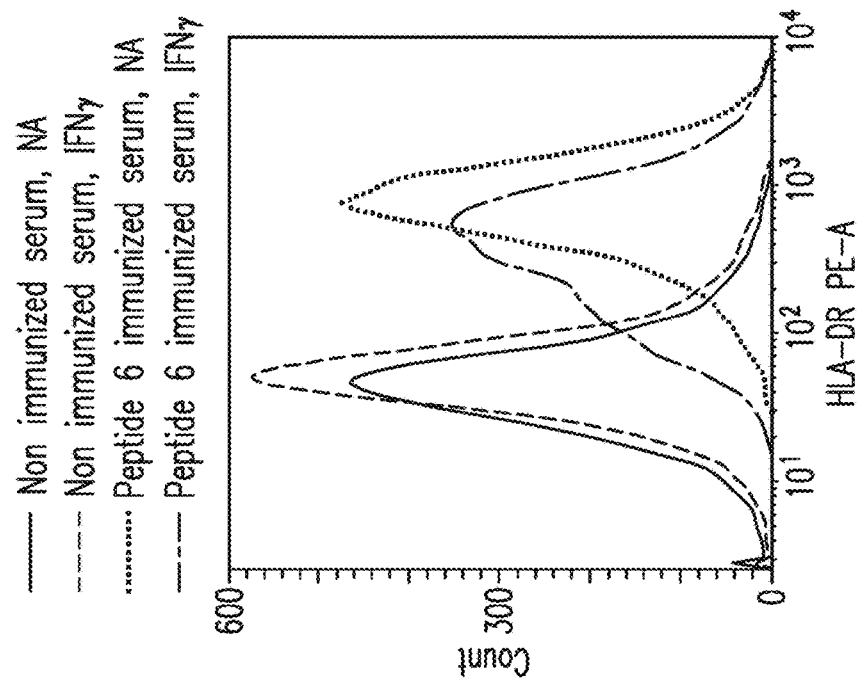
Fig. 13b(2)
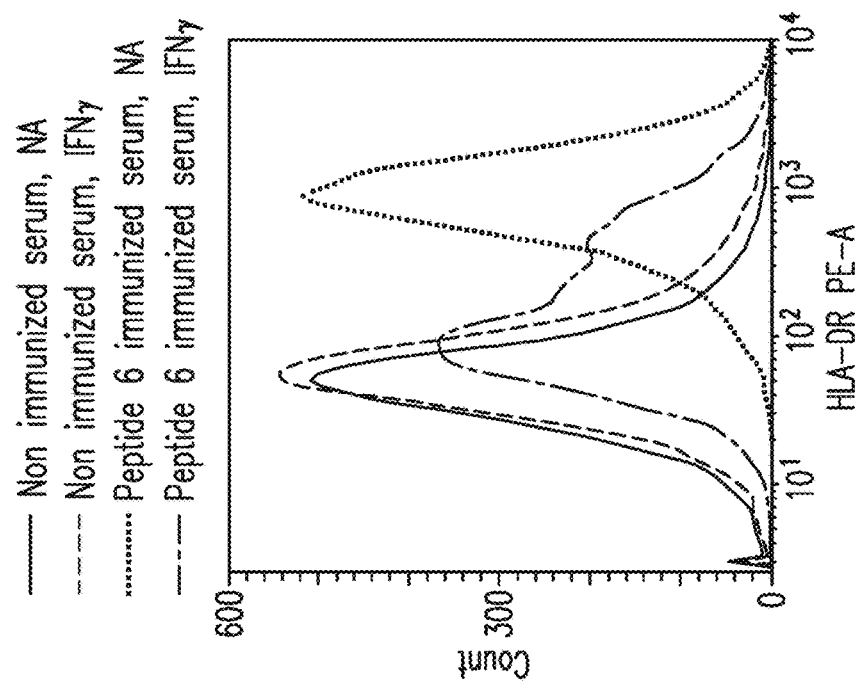
Fig. 13b(1)

SEQUENCE LISTING

```
<160> NUMBER OF SEQ ID NOS: 39

<210> SEQ ID NO 1
<211> LENGTH: 7
<212> TYPE: PRT
<213> ORGANISM: Mus musculus

<400> SEQUENCE: 1

Leu Pro Glu Ser Ser Leu Arg
1               5

<210> SEQ ID NO 2
<211> LENGTH: 30
<212> TYPE: PRT
<213> ORGANISM: Homo sapiens

<400> SEQUENCE: 2

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu
            20                  25                  30

<210> SEQ ID NO 3
<211> LENGTH: 30
<212> TYPE: PRT
<213> ORGANISM: Homo sapiens

<400> SEQUENCE: 3

Asp Asn Gly Thr Leu Phe Leu Gly Ile Leu Lys Asn Trp Lys Glu Glu
1               5                   10                  15

Ser Asp Arg Lys Ile Met Gln Ser Gln Ile Val Ser Phe Tyr
            20                  25                  30

<210> SEQ ID NO 4
<211> LENGTH: 30
```

<212> TYPE: PRT
<213> ORGANISM: Homo sapiens

<400> SEQUENCE: 4

```
Ser Gln Ile Val Ser Phe Tyr Phe Lys Leu Phe Lys Asn Phe Lys Asp
1               5                   10                  15
Asp Gln Ser Ile Gln Lys Ser Val Glu Thr Ile Lys Glu Asp
            20                  25                  30
```

<210> SEQ ID NO 5
<211> LENGTH: 30
<212> TYPE: PRT
<213> ORGANISM: Homo sapiens

<400> SEQUENCE: 5

```
Val Glu Thr Ile Lys Glu Asp Met Asn Val Lys Phe Phe Asn Ser Asn
1               5                   10                  15
Lys Lys Lys Arg Asp Asp Phe Glu Lys Leu Thr Asn Tyr Ser
            20                  25                  30
```

<210> SEQ ID NO 6
<211> LENGTH: 30
<212> TYPE: PRT
<213> ORGANISM: Homo sapiens

<400> SEQUENCE: 6

```
Phe Glu Lys Leu Thr Asn Tyr Ser Val Thr Asp Leu Asn Val Gln Arg
1               5                   10                  15
Lys Ala Ile His Glu Leu Ile Gln Val Met Ala Glu Leu Ser
            20                  25                  30
```

<210> SEQ ID NO 7
<211> LENGTH: 30
<212> TYPE: PRT
<213> ORGANISM: Homo sapiens

<400> SEQUENCE: 7

```
Ile Gln Val Met Ala Glu Leu Ser Pro Ala Ala Lys Thr Gly Lys Arg
1               5                   10                  15
Lys Arg Ser Gln Met Leu Phe Arg Gly Arg Arg Ala Ser Gln
            20                  25                  30
```

<210> SEQ ID NO 8
<211> LENGTH: 7
<212> TYPE: PRT
<213> ORGANISM: Homo sapiens

<400> SEQUENCE: 8

```
Pro Tyr Val Lys Glu Ala Glu
1               5
```

<210> SEQ ID NO 9
<211> LENGTH: 8
<212> TYPE: PRT
<213> ORGANISM: Homo sapiens

<400> SEQUENCE: 9

```
Ala Gly His Ser Asp Val Ala Asp
1               5
```

<210> SEQ ID NO 10
<211> LENGTH: 7
<212> TYPE: PRT

<213> ORGANISM: Homo sapiens

<400> SEQUENCE: 10

Lys Glu Glu Ser Asp Arg Lys
1               5

<210> SEQ ID NO 11
<211> LENGTH: 8
<212> TYPE: PRT
<213> ORGANISM: Homo sapiens

<400> SEQUENCE: 11

Lys Asp Asp Gln Ser Ile Gln Lys
1               5

<210> SEQ ID NO 12
<211> LENGTH: 4
<212> TYPE: PRT
<213> ORGANISM: Homo sapiens

<400> SEQUENCE: 12

Glu Thr Ile Lys
1

<210> SEQ ID NO 13
<211> LENGTH: 9
<212> TYPE: PRT
<213> ORGANISM: Homo sapiens

<400> SEQUENCE: 13

Asn Lys Lys Lys Arg Asp Asp Phe Glu
1               5

<210> SEQ ID NO 14
<211> LENGTH: 10
<212> TYPE: PRT
<213> ORGANISM: Homo sapiens

<400> SEQUENCE: 14

Ser Pro Ala Ala Lys Thr Gly Lys Arg Lys
1               5                   10

<210> SEQ ID NO 15
<211> LENGTH: 16
<212> TYPE: PRT
<213> ORGANISM: Bos taurus

<400> SEQUENCE: 15

Val Met Asn Asp Leu Ser Pro Lys Ser Asn Leu Arg Lys Arg Lys Arg
1               5                   10                  15

<210> SEQ ID NO 16
<211> LENGTH: 16
<212> TYPE: PRT
<213> ORGANISM: Equus caballus

<400> SEQUENCE: 16

Val Met Asn Asp Leu Ser Pro Lys Ala Asn Leu Arg Lys Arg Lys Arg
1               5                   10                  15

<210> SEQ ID NO 17
<211> LENGTH: 16
<212> TYPE: PRT
<213> ORGANISM: Sus scrofa

```
<400> SEQUENCE: 17

Val Met Asn Asp Leu Ser Pro Arg Ser Asn Leu Arg Lys Arg Lys Arg
1               5                   10                  15

<210> SEQ ID NO 18
<211> LENGTH: 15
<212> TYPE: PRT
<213> ORGANISM: Gallus gallus

<400> SEQUENCE: 18

Ile Leu Gln Lys Leu Val Asp Pro Pro Ser Phe Lys Arg Lys Arg
1               5                   10                  15

<210> SEQ ID NO 19
<211> LENGTH: 16
<212> TYPE: PRT
<213> ORGANISM: Mus musculus

<400> SEQUENCE: 19

Val Val His Gln Leu Leu Pro Glu Ser Ser Leu Arg Lys Arg Lys Arg
1               5                   10                  15

<210> SEQ ID NO 20
<211> LENGTH: 16
<212> TYPE: PRT
<213> ORGANISM: Homo sapiens

<400> SEQUENCE: 20

Val Met Ala Glu Leu Ser Pro Ala Ala Lys Thr Gly Lys Arg Lys Arg
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: EE-IFNr

<400> SEQUENCE: 21

Val Met Ala Glu Leu Leu Pro Glu Ser Ser Leu Arg Lys Arg Lys Arg
1               5                   10                  15

<210> SEQ ID NO 22
<211> LENGTH: 13
<212> TYPE: PRT
<213> ORGANISM: Homo sapiens

<400> SEQUENCE: 22

Ala Ala Lys Thr Gly Lys Arg Lys Arg Ser Gln Met Leu
1               5                   10

<210> SEQ ID NO 23
<211> LENGTH: 11
<212> TYPE: PRT
<213> ORGANISM: Aspergillus terreus

<400> SEQUENCE: 23

Thr Pro Gly Lys Arg Lys Arg Ser Glu Gln Gln
1               5                   10

<210> SEQ ID NO 24
<211> LENGTH: 14
<212> TYPE: PRT
<213> ORGANISM: Aspergillus fumigatus
```

<400> SEQUENCE: 24

Thr Pro Lys Ile Thr Gly Lys Arg Lys Arg Ser Glu Glu Gln
1               5                   10

<210> SEQ ID NO 25
<211> LENGTH: 13
<212> TYPE: PRT
<213> ORGANISM: Aspergillus flavus

<400> SEQUENCE: 25

Thr Pro Lys Thr Gly Lys Arg Lys Arg Thr Glu Glu Gln
1               5                   10

<210> SEQ ID NO 26
<211> LENGTH: 13
<212> TYPE: PRT
<213> ORGANISM: Aspergillus nidulans

<400> SEQUENCE: 26

Ser Pro Lys Ile Gly Lys Arg Lys Arg Ser Glu Thr Gln
1               5                   10

<210> SEQ ID NO 27
<211> LENGTH: 13
<212> TYPE: PRT
<213> ORGANISM: Aspergillus niger

<400> SEQUENCE: 27

Thr Pro Lys Ile Gly Lys Arg Lys Arg Ser Asp Glu Gln
1               5                   10

<210> SEQ ID NO 28
<211> LENGTH: 13
<212> TYPE: PRT
<213> ORGANISM: Cryptococcus neoformans

<400> SEQUENCE: 28

Leu Gly Ser Thr Gly Lys Arg Lys Arg Ser Ser Met Gly
1               5                   10

<210> SEQ ID NO 29
<211> LENGTH: 11
<212> TYPE: PRT
<213> ORGANISM: Mycobacterium intracellulare

<400> SEQUENCE: 29

Asn Pro Ala Gly Gly Lys Arg Lys Arg Ser Gln
1               5                   10

<210> SEQ ID NO 30
<211> LENGTH: 13
<212> TYPE: PRT
<213> ORGANISM: Clostridium sp.

<400> SEQUENCE: 30

Lys Glu Gln Ser Lys Lys Arg Lys Arg Ser Gln Met Thr
1               5                   10

<210> SEQ ID NO 31
<211> LENGTH: 13
<212> TYPE: PRT
<213> ORGANISM: Rattus norvegicus

<400> SEQUENCE: 31

Cys Thr Pro Lys Thr Gly Lys Arg Lys Arg Ser Glu Gln
1               5                   10

<210> SEQ ID NO 32
<211> LENGTH: 13
<212> TYPE: PRT
<213> ORGANISM: Rattus norvegicus

<400> SEQUENCE: 32

Cys Ala Ala Lys Thr Gly Lys Arg Lys Arg Ser Gln Met
1               5                   10

<210> SEQ ID NO 33
<211> LENGTH: 11
<212> TYPE: PRT
<213> ORGANISM: Homo sapiens

<400> SEQUENCE: 33

Ser Pro Ala Ala Lys Thr Gly Lys Arg Lys Arg
1               5                   10

<210> SEQ ID NO 34
<211> LENGTH: 15
<212> TYPE: PRT
<213> ORGANISM: Homo sapiens

<400> SEQUENCE: 34

Ser Pro Ala Ala Lys Thr Gly Lys Arg Lys Arg Ser Gln Met Leu
1               5                   10                  15

<210> SEQ ID NO 35
<211> LENGTH: 20
<212> TYPE: PRT
<213> ORGANISM: Aspergillus terreus

<400> SEQUENCE: 35

Lys Lys Asp Val Pro Pro Lys Thr Gly Lys Arg Lys Arg Ser Glu Gln
1               5                   10                  15

Gln Lys Asp Glu
            20

<210> SEQ ID NO 36
<211> LENGTH: 7
<212> TYPE: PRT
<213> ORGANISM: Aspergillus terreus

<400> SEQUENCE: 36

Lys Thr Gly Lys Arg Lys Arg
1               5

<210> SEQ ID NO 37
<211> LENGTH: 6
<212> TYPE: PRT
<213> ORGANISM: Homo sapiens

<400> SEQUENCE: 37

Thr Gly Lys Arg Lys Arg
1               5

<210> SEQ ID NO 38
<211> LENGTH: 4
<212> TYPE: PRT
<213> ORGANISM: Artificial Sequence
<220> FEATURE:
<223> OTHER INFORMATION: EE-IFNr -continued

```
<400> SEQUENCE: 38

Lys Arg Lys Arg
1

<210> SEQ ID NO 39
<211> LENGTH: 7
<212> TYPE: PRT
<213> ORGANISM: Homo sapiens

<400> SEQUENCE: 39

Ser Pro Ala Ala Lys Thr Gly
1               5
```

EPITOPE RECOGNIZED BY ANTI-INTERFERON GAMMA AUTOANTIBODIES IN PATIENTS WITH DISSEMINATED MYCOBACTERIAL INFECTIONS AND THE APPLICATION THEREFOR

CROSS-REFERENCE TO RELATED APPLICATION AND CLAIM OF PRIORITY

The application claims the benefit of Taiwan Application No. 104119897, filed on Jun. 22, 2015, at the Taiwan Intellectual Property Office, the disclosures of which are incorporated herein in their entirety by reference.

FIELD OF THE INVENTION

The invention is related to a medical, dental or toilet preparation. In particular, it is related to the preparation of one kind of peptide fragments, which can be used in patients suffering from a disseminated mycobacterial infection.

BACKGROUND OF THE INVENTION

Anticytokine autoantibodies (ACADs) are increasingly recognized, and playing an important role in the pathogenesis of infectious and autoimmune diseases.

Clinically, the pathogenic mycobacterial species can cause tuberculosis, Hansen's disease, leprosy, pulmonary disease, lymphadenitis and skin disease. In view of mycobacterial immunity, $IFN_r$ plays an important role and is mainly produced by T and NK cells when stimulated with microbial products.

Genetic defects in the $IFN_r$/IL-12 pathway cause Mendelian susceptibility to mycobacterial diseases (MSMDs) in young patients with disseminated mycobacterial infections.

On the other hand, interference with the $IFN_r$ signaling by the presence of anti-$IFN_r$ AutoAbs is the major etiology that explains the occurrence of severe disseminated mycobacterial infections in adults without obvious immunologic defects, in particular for patients from the Southeast Asia.

The similarity of clinical susceptibility to MSMDs strongly suggests that AutoAbs against $IFN_r$ were the cause rather than a consequence of mycobacterial infection.

The mechanism of the production of anti-$IFN_r$ AutoAbs also remains unclear. Restriction of the disease in Southeast Asian population suggest that a particular genetic factor and mechanism are involved.

According to a previous study, HLA class II molecules DRB1*16:02 and HLA-DQB1*05:02 are the two specific alleles strongly associated with this disease, and the high frequency of this allele in Southeast Asia might also explain the susceptibility of anti-$IFN_r$ AutoAbs in this particular population.

MHC class II is present the particular peptides to CD4$^+$ T cells to induce an adaptive immune response and is a strong genetic factor associated with autoimmune diseases. It seems that particular pathogenic peptide fragments present in these particular HLA alleles are involved in the production of anti-$IFN_r$ AutoAbs.

Various hypotheses have been proposed to explain the production of these pathogenic AutoAbs. Molecular mimicry theory states that exo-antigen can mimic self-antigen and induces the formation of AutoAbs. This theory, molecular mimicry, has been documented in various autoimmune diseases, including multiple sclerosis (MS), ankylosing spondylitis, Graves' disease, diabetes mellitus, and systemic lupus erythematosus (SLE).

In the case of MS and SLE, the disease pathogenesis has been linked to some viruses, such as the Epstein-Barr virus (EBV), for their homologous amino acid sequences with human antigenic structures in the central nerve system or lupus autoantigens, such as Sm B.

These findings suggest that molecular mimicry plays a major role in the pathogenesis of certain diseases. Despite advances in the genomic technologies for autoimmunity, the precise mechanism for the pathogenic AutoAbs formation is still unclear.

SUMMARY OF THE INVENTION

Autoantibodies (AutoAbs) against $IFN_r$ is an emerging medical issue and linked to disseminated mycobacterial infections and other opportunistic infections in the Southeast Asia. The origin of these AutoAbs is unclear; however, the majority of affected patients share specific HLA class II alleles and this observation suggests that a common mechanism in the production of AutoAbs may exist. Herein, the inventor characterized the anti-$IFN_r$ AutoAbs from patients and found these AutoAbs recognized a major epitope ($P_{121-131}$) in the C-terminal of $IFN_r$. The region was known to be critical for $IFN_r$ receptor activation, and the inventor also demonstrated that AutoAbs to this epitope had a neutralizing activity. This epitope was 100% homologous to the *Aspergillus* Noc2 and anti-$IFN_r$ AutoAbs from patients could react with this epitope and *Aspergillus* Noc2. In vivo study, rats immunized with *Aspergillus* Noc2 developed antibodies against human $IFN_r$ and vice versa.

In addition, the inventor generated an epitope Erase $IFN_r$ (EE-$IFN_r$) which has lower affinity recognized by anti-$IFN_r$ AutoAbs due to a modified major epitope region and it could activate the $IFN_r$ downstream signaling pathway ex vivo even in the presence of anti-$IFN_r$ AutoAbs.

It was found that anti-$IFN_r$ •AutoAbs from different patients recognized a specific region, SPAAKTGKRK (SEQ ID NO: 14), in the C-terminal of $IFN_r$ and these antibodies had a neutralizing activity on $IFN_r$.

A high homologous peptide sequence in this region (KTGKRKR (SEQ ID NO: 36)) was found in *Aspergillus* Noc2 and also recognized by the anti-$IFN_r$ AutoAbs.

After immunization with *Aspergillus* Noc2, antibodies against human $IFN_r$ • were formed in the test rats.

Furthermore, the inventor used a mouse homologous region to replace the critical anti-$IFN_r$ •AutoAb-recognized epitope in human $IFN_r$□ and generated a new recombinant protein, epitope Erased $IFN_r$ •(EE-$IFN_r$).

This recombinant protein could induce the activation of the $IFN_r$ receptor, even in the presence of anti-$IFN_r$ •AutoAbs ex vivo.

Taken together, the results suggest that anti-$IFN_r$ •AutoAbs may be induced by the means of molecular mimicry, and structural modification of $IFN_r$ • can bypass the blocking activity of anti-$IFN_r$ •AutoAbs.

In accordance with one aspect of the present invention, a method for evaluating an efficacy of an isolated recombinant human interferon gamma (h$IFN_r$) for regulating a peripheral blood mononuclear cell (PBMC) is disclosed. The method comprises the steps of: providing the PBMC from a subject with anti-interferon gamma autoantibodies; mixing the isolated recombinant human interferon gamma with the PBMC, wherein the isolated recombinant human interferon gamma contains a homologous substitute; and evaluating the efficacy of the isolated recombinant human interferon gamma according to an expression level of a phosphorylation of signal transducers and activators of transcription 1 (p-STAT1) generated by the PBMC.

In accordance with another aspect of the present invention, a method for evaluating an efficacy of an isolated recombinant cytokine for regulating a peripheral blood mononuclear cell (PBMC) is disclosed. The method comprises steps of: providing the PBMC from a subject with an anticytokine autoantibody; mixing the isolated recombinant cytokine with the PBMC, wherein the isolated recombinant cytokine contains a homologous substitute; and evaluating the efficacy of the isolated recombinant cytokine according to an expression level of an interleukin-12 (IL-12) generated by the PBMC.

In accordance with another aspect of the present invention, a recombinant protein is disclosed. The recombinant protein comprises: a human interferon gamma having a sequence replaced with a peptide of "Leu-Pro-Glu-Ser-Ser-Leu-Arg" (SEQ NO: 1), wherein the recombinant protein is used to activate a receptor of an interferon gamma ($IFN_r$) and is free from neutralization by an autoantibody of the interferon gamma of a subject suffering from a disseminated mycobacterial infection.

BRIEF DESCRIPTION OF THE DRAWINGS

FIGS. 1a-1h illustrate AutoAbs to $IFN_r$ recognized C-terminal region of $IFN_r$ according to the embodiment of the present invention;

FIGS. 2a-2e illustrate epitope Erase $IFN_r$ according to the embodiment of the present invention;

FIGS. 3a-3g demonstrate molecular mimicry;

FIGS. 4a-4h illustrate epitope Erase $IFN_r$ and the application therefor according to the embodiment of the present invention;

FIG. 5 illustrates IFN$_r$ direct ELIAS used to detect AutoAbs against IFN$_r$;

FIGS. 6a-6b illustrate that IL-12 production levels and IFN$_r$ production levels were measured by ELISA;

FIG. 7 illustrates the result of epitope mapping;

FIG. 8 illustrates the result of Western blot analysis conducted on various recombinant interferons;

FIG. 9 illustrates the results of probing plasma sampled from IFN$_r$ AutoAbs patients and healthy controls;

FIG. 10 illustrates the results of protein mapping;

FIGS. 11a-11b illustrate the results of plasma interacting with hIFN$_r$ and mIFN$_r$;

FIG. 12 illustrates the results of Western blot analysis conducted on different various recombinant Noc2 proteins; and FIGS. 13a-13b illustrate the results of p-STAT-1 expression levels and HLA-DR expression levels.

DETAILED DESCRIPTION OF THE PREFERRED EMBODIMENTS

The present invention will now be described more specifically with reference to the following embodiments. It is to be noted that the following descriptions of preferred embodiments of this invention are presented herein for the purposes of illustration and description only; they are not intended to be exhaustive or to be limited to the precise form disclosed.

[Patients and Definitions]

All participants were adults (age >20 years) and were followed regularly at medical centers in Taiwan. Disseminated mycobacterial infection was diagnosed if patients presented 2 or more noncontiguous places and positive blood or BM cultures. The diagnosis of pulmonary NTM infection was based on the criteria proposed by the American Thoracic Society and Infectious Diseases Society of America. The study was approved by the Institutional Review Board of China Medical University Hospital (DMR98-IRB-261) and Chang Gung Memorial Hospital (103-2861C), and informed written consent was obtained from all of the patients in accordance with the Declaration of Helsinki.

[Reagents]

The inventor used the following monoclonal antibodies: anti-human IFN$_r$ (clone EPR1108, Abcam), anti-V5 tag (clone SV5-Pk1, Abcam), FITC mouse anti-human CD14 (clone M5E2, BD Pharmingen), PE mouse anti-human Human Leukocyte Antigen-antigen D Related (HLA-DR) (clone G46-6, BD Pharmingen) and PE Mouse Anti-Stat1 (pY701) (clone 4a, BD Phosflow).

[Detection and Titration of IFN$_r$ Neutralizing Autoantibodies]

Blood plasma from patients and donors was serially diluted ($10^{-1}$ to $10^{-6}$) and incubated with recombinant human IFN$_r$ at a final concentration of 200 pg/mL for 1 hour at 37° C. The IFN$_r$ level was measured with a human IFN$_r$ ELISA kit from BD Biosciences according to the manufacturer's recommendations. All experiments were performed in duplicate.

[Peptide Synthesis]

All peptides were synthesized by Kelowna International Scientific Inc., Taiwan. The peptides were lyophilized, and the purity and mass were assessed by high-performance liquid chromatography and mass spectrometry, respectively.

[Epitope Mapping]

Clear polystyrene 96-well flat bottom plates (Nunc) were coated with 100 μL of peptide solution (5 μg/mL) with b-carbonate buffer (pH 9.6) at 4° C. overnight. After blocking the remaining binding sites with 5% human normal serum albumin (Aventis) in PBS, the plates were incubated at 37° C. for 1 hour. Afterward, the plates were washed 3 times with 0.5% Tween 20 in PBS.

Blood plasma samples were added at a 1:100 dilution, in PBS containing 5% human normal serum albumin. Following incubation at room temperature for 2 hours and being washed 3 times, goat anti-human IgG Fc$_r$ fragment specific conjugated with alkaline phosphate (Jackson ImmunoResearch Laboratories), was added at a 1:5000 dilution, and the plates were kept for 1 hour at room temperature. Finally, after being washed 5 times, 100 μL of p-Nitrophenyl Phosphate (pNPP) was added and the reaction was read at 405 nm by a VICTOR X3 Multilabel Plate Reader (PerkinElmer) after 30 minutes of incubation at 37° C.

[Competition Enzyme-Linked Immunosorbent Assay (ELISA)]

To evaluate the specificity of the reaction, a competition ELISA experiment was performed. Each plasma sample (1:100 dilutions) was pre-incubated with different concentrations (5-30 μg/mL) of the competition peptides overnight at 4° C. Subsequently, all plasma and different concentrations competition peptides mixture samples were examined following the epitope mapping protocol. Peptide 6 was coated with b-carbonate buffer (pH 9.6) at 4° C. overnight. After blocking at 37° C. for 1 hour, all pre-incubated plasma and different concentrations competition peptides mixture samples were added in duplicate. Following 2 hours of room temperature incubation, goat anti-human IgG Fc$_r$ fragment specific conjugated with alkaline phosphate, was added.

Figure 1D:
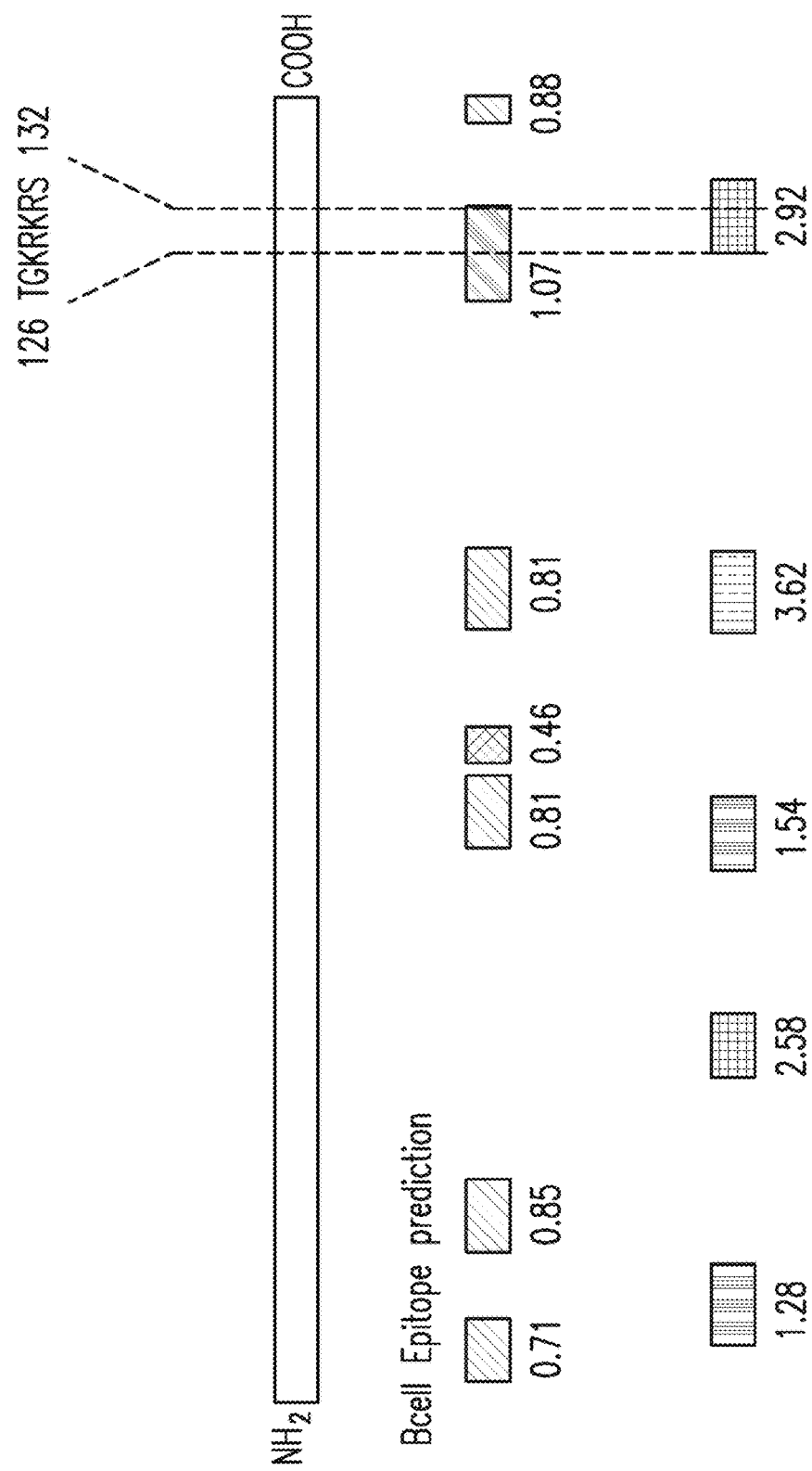

Finally, 100 μL of pNPP was added and the reaction was read at 405 nm by a VICTOR X3 Multilabel Plate Reader (PerkinElmer) after 30 minutes of incubation at 37° C.

[Prediction of B Cell Epitopes]

The prediction of B cell epitopes was carried out using BepiPred Linear epitope Prediction and Emini Surface Accessibility Prediction. The software takes a single sequence in FASTA format as an input. BepiPred predicts the location of linear B-cell epitopes using a combination of a hidden Markov model and a propensity scale method. In Emini Surface Accessibility Prediction, the calculation was based on surface accessibility scale of a product instead of an addition within the window. The accessibility profile was obtained using a special formula.

[Generation of Recombinant Human $IFN_r$]

The inventor amplified the $IFN_r$• from base 196 to 624 of the open reading frame (ORF) by polymerase chain reaction (PCR) and cloned it into pMT/BiP/V5-His (Invitrogen) for *Drosophila* Schneider 2 (S2) cells expression. Recombinant $IFN_r$• was further purified by V5 tagged protein purification kit (MBL). The mutated recombinant $IFN_r$• was performed by QuickChange Site-Directed Mutagenesis kit (Stratagene). The inventor confirmed the sequences and cloning sites of all constructs as well as the size and immunoreactivity of the recombinant $IFN_r$• by Western Blot.

[Generation of Recombinant *Aspergillus* Noc2]

The inventor amplified the Noc2 from base 1 to 2361 of the ORF by PCR and cloned it into pMT/BiP/V5-His (Invitrogen) for S2 cells expression. Recombinant Noc2 were further purified by a V5 tagged protein purification kit (MBL). Then, the sequences and cloning sites of all constructs were confirmed as well as the size and immunoreactivity of recombinant Noc2 by Western Blot.

[p-STAT1 Intracellular Stain]

A total of $10^6$ PBMCs in 200 μL RPMI-1640 with 10% FBS and 1% penicillin/streptomycin was used. Cells were then stimulated with 500 IU $IFN_r$, $IFN_r$ 1-131 or EE-$IFN_r$□ in 160 μL RPMI-1640 pre-incubated with 40 μL of normal plasma or patient plasma for 10 min at room temperature. After 30 minutes of stimulation in a 37° C. incubator, monocytes were identified by FITC-CD14 (BD Pharmingen) surface staining. Fixed by adding 250 μL of FASC lysing solution (BD Pharmingen) and incubated at room temperature for 15 minutes in the dark, followed by two washes with PBS. To permeabilize the cells, 500 μl of ice-cold absolute methanol was added to each tube and incubated for 15 minutes on ice in the dark, followed by two washes with PBS. Next, PE-phospho-STAT1 (pY701) antibody (BD Pharmingen) was added, followed by 30 minutes incubation on ice in the dark. Again, cells were washed with 2 mL of PBS before resuspension in the 500 μL of PBS. Data were collected with a FACSVerse flow cytometer (BD Biosciences) and analyzed using FACSuite software (BD Biosciences).

[Immunoblotting]

Recombinant $IFN_r$□ (R&D Systems) and different truncated forms of recombinant $IFN_r$□ were subjected to SDS-PAGE using a 10% gel under reducing conditions at 120 V for 2 hours. The proteins were transferred to a PVDF membrane (Invitrogen Life Technologies) at 250 mA for 2 hours. The membrane was blocked in 5% human normal serum albumin (Aventis) in TBS with 0.1% Tween 20 overnight at 4° C. The membrane was incubated with a 1/100 dilution of patient or control blood plasma for 3 hours at room temperature. After being washed three times, the membrane was incubated in a 1/10,000 dilution of mouse anti-human IgG conjugated with horseradish peroxidase (Jackson ImmunoResearch Laboratories) for 1 hour at room temperature. After being washed three times, the membrane was developed with ECL (Merck Millipore).

[HLA-DR Expression]

A total of $10^6$ PBMCs in 200 μL RPMI-1640 with 10% FBS and 1% penicillin/streptomycin was used. Cells were then stimulated with 500 IU $IFN_r$, $IFN_r$ 1-131 or EE-$IFN_r$• in 160 μL RPMI-1640 pre-incubated with 40 μL of normal blood plasma or patient blood plasma for 10 min at room temperature. After 24 hours of stimulation in a 37° C. incubator, monocytes were identified by FITC-CD14 (BD Pharmingen) surface staining. Next, PE-HLA-DR antibody (BD Pharmingen) was added followed by 30 minutes of incubation on ice in the dark. Cells were again washed with 2 ml of PBS before resuspension in 500 μl of PBS. Data were collected with a FACSVerse flow cytometer (BD Biosciences) and analyzed using FACSuite software (BD Biosciences).

Immunization with Noc2 or $IFN_r$• Peptide

The inventor immunized WKY/NcrlNarl rats with 0.25 mg Noc2 or $IFN_r$□ peptide (Noc2: CTPKTGKRKRSEQ (SEQ NO: 31); $IFN_r$: CAAKTGKRKRSQM (SEQ NO: 32)) conjugated with ovalbumin (OVA) and gave a booster dose every two weeks after the initial injection (day 0). After 70 days, the inventor checked the antibody production level by dot blot or ELISA at each injection. All rats were sacrificed ten days after the tenth injection (day 136) and whole blood was collected. After collection of the whole blood, the blood was allowed to clot by leaving it undisturbed at room temperature 15 minutes. Clots were removed by centrifuging at 1500 g for 10 minutes in a refrigerated centrifuge. Sera were aliquoted and stored at −20° C. for further use.

[Experimental Data]

Please refer to FIGS. 1*a*-1*h*, which are related to AutoAbs to $IFN_r$, recognized C-terminal region of $IFN_r$.

FIG. 1*a* demonstrates amino acid sequences of human $IFN_r$•30-mer overlapping synthetic peptides.

FIG. 1*b*(1)-FIG. 1*b*(6) demonstrate epitope mapping for determining serum binding affinity of the synthetic peptide to $IFN_r$, represented as the mean optical density (OD) at 405 nm; plasma sample from $IFN_r$, AutoAbs patients (n=15), Mycobacteria infected patients (n=2) and healthy controls (n=6).

FIG. 1*c*(1)-FIG. 1*c*(2) demonstrate the inhibition using ELISA, wherein each plasma sample from $IFN_r$•AutoAbs patients was pre-incubated with different concentrations of a control peptide or peptide 6, and then all plasma dilutions were examined by ELISA for reactivity against peptide 6.

FIG. 1*d* demonstrates a schematic diagram of $IFN_r$, and the prediction scores for linear B cell epitopes and surface acceptability regions. Each green bar represents a predicted B cell epitope, and each red bar represents a predicted surface acceptable region. The prediction scores represent the average scores for all amino acids within the region with prediction values above the cut-offs chosen for significance. The bar color intensities are proportional to the prediction scores found.

Figure 1E:
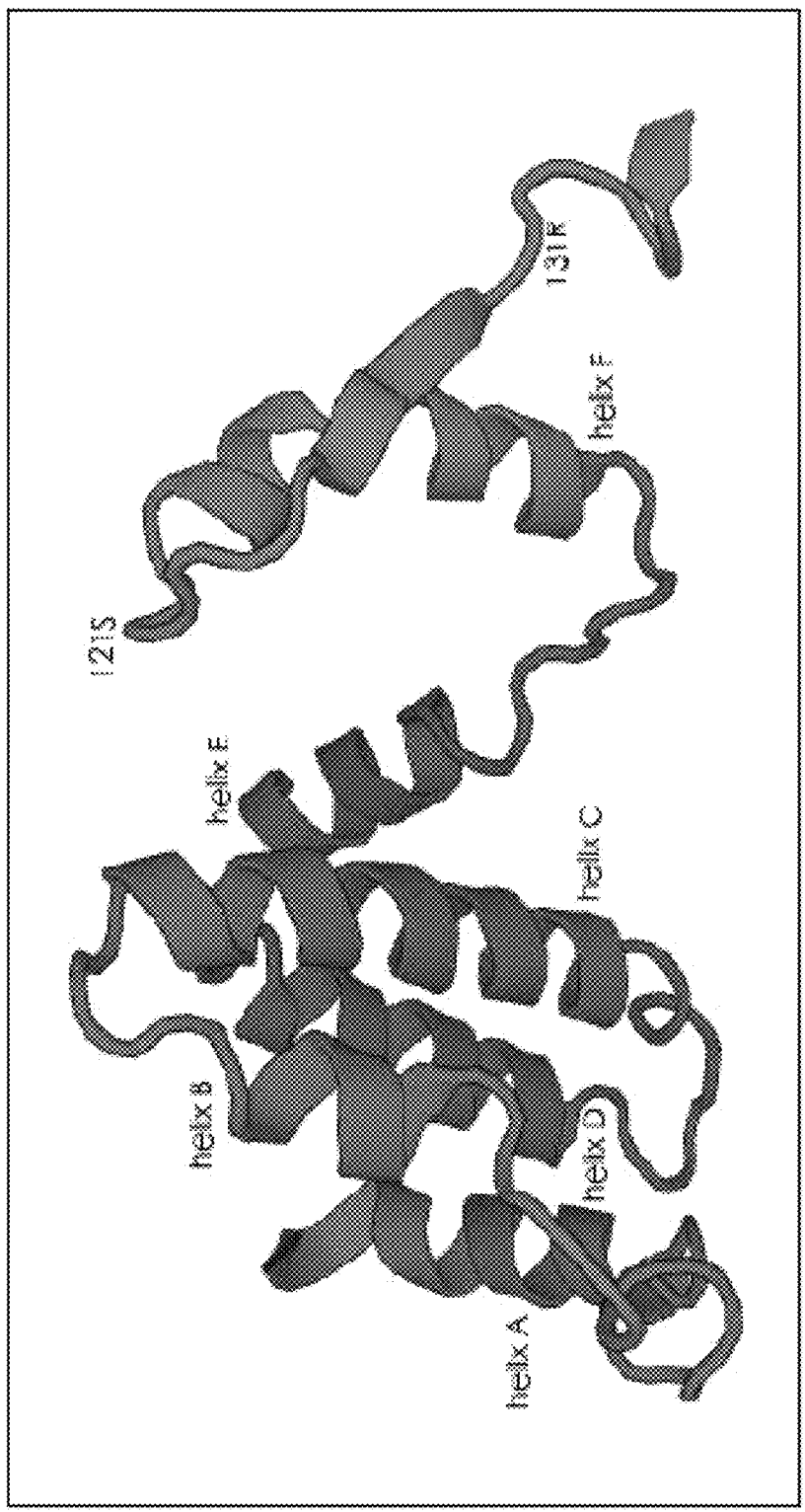

FIG. 1*e* demonstrates a three-dimensional projection of the structure of $IFN_r$. The epitope, amino acids 121-131 of $IFN_r$• are located at the C-terminal and extend into the solvent.

Figure 1F:
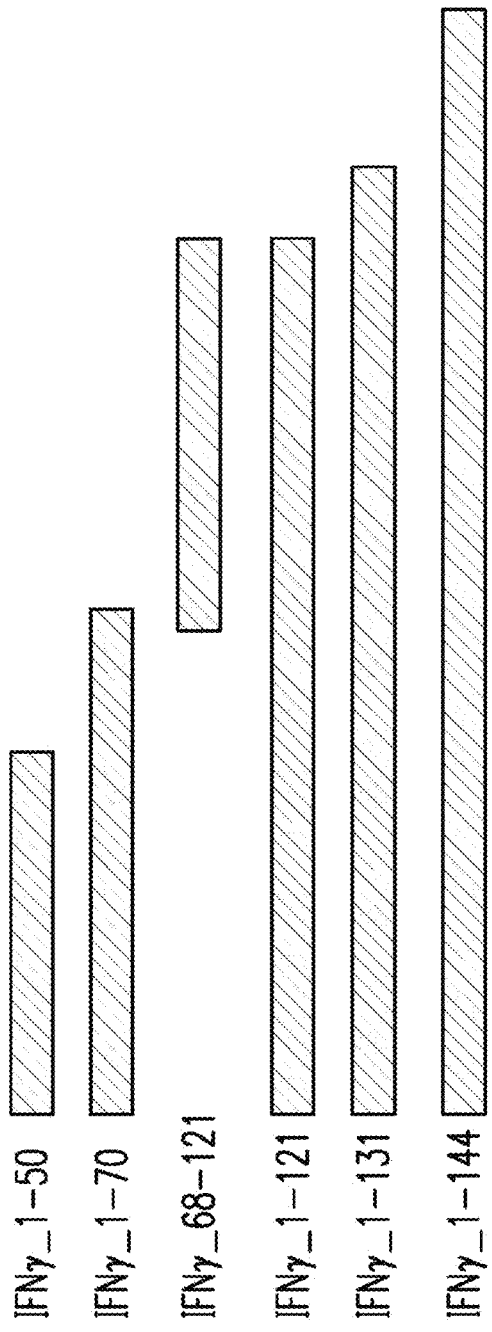

FIG. 1*f* demonstrates a graphical representation of the different length of truncated recombinant $IFN_r$ proteins.

FIG. 1*g*(1)-FIG. 1*g*(6) demonstrate protein mapping used to determine plasma binding affinity of the recombinant proteins to $IFN_r$, represented as the mean optical density (OD) at 405 nm; plasma sample from IFN$_r$•AutoAbs patients (n=16), Mycobacteria infected patients (n=2) and healthy controls (n=3).

Figure 1H:
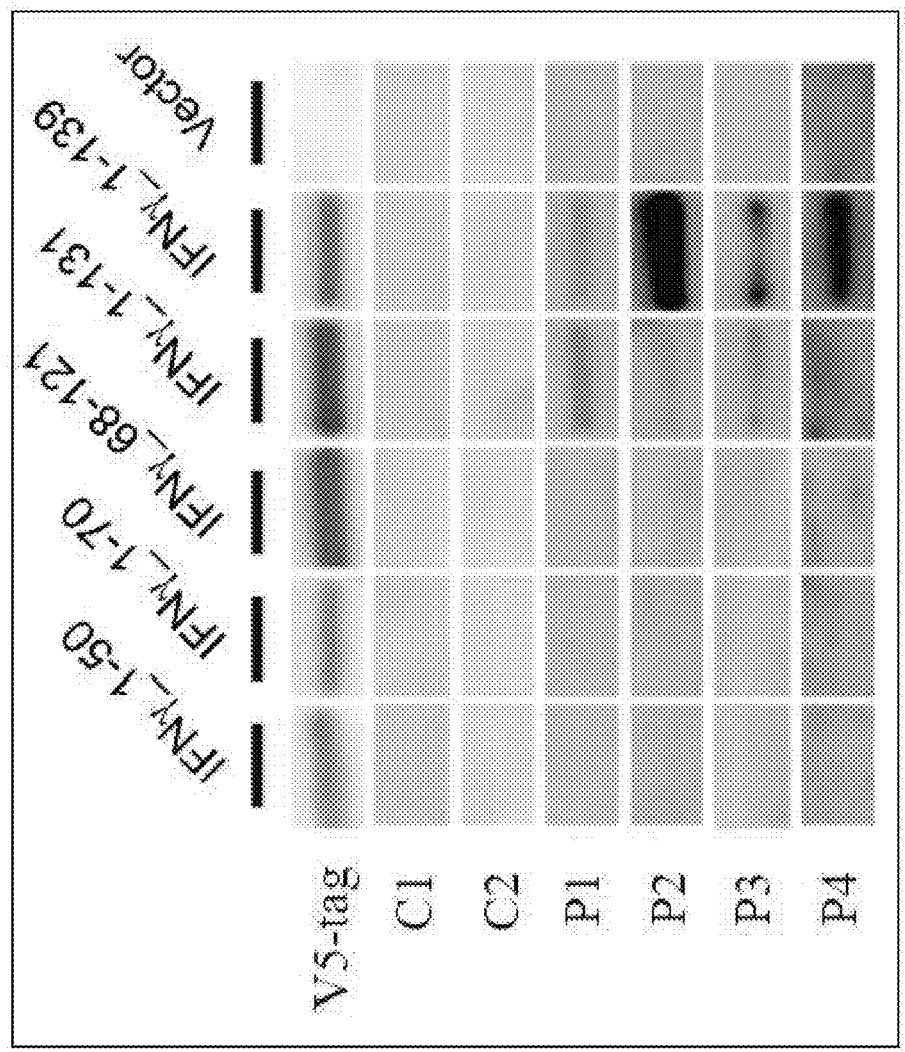

FIG. 1h demonstrates a Western blot showing binding ability of blood plasma from IFN$_r$•AutoAbs patients (n=4, P1-4) and healthy controls (n=2, C1-2) to different truncated forms of IFN$_r$.

Please refer to Table 1, which demonstrates multiple amino acid sequence alignments of IFN$_r$ in different species and EE-IFN$_r$ (SEQ NO: 15-21). The conserved residues in the other species are boxed. The sequence of EE-IFN$_r$ protein, which has substituted human P$_{121-127}$ Ser-Pro-Ala-Ala-Lys-Thr-Gly (SPAAKTG) (SEQ ID NO: 39) with homologous murine Leu-Pro-Glu-Ser-Ser-Leu-Arg (LPESSLR) addressing SEQ NO: 1 are in bold.

TABLE 1

|  | 116   121   127 |  |
|---|---|---|
| B. taurus | VMNDLSPKSNLRKRKR | (SEQ ID NO: 15) |
| E. caballus | VMNDLSPKANLRKRKR | (SEQ ID NO: 16) |
| S. scrofa | VMNDLSPRSNLRKRKR | (SEQ ID NO: 17) |
| G. gallus | ILQKLVDPP-SFKRKR | (SEQ ID NO: 18) |
| M. musculus | CCHQLLPESSLRKRKR | (SEQ ID NO: 19) |
| H. sapiens | VMAELSPAAKTGKRKR | (SEQ ID NO: 20) |
| EE-IFNγ | VMAELLPESSLRKRKR | (SEQ ID NO: 21) |

In other embodiments, it is possible to apply homologous substitutes with various peptide lengths to replace the sequence in human P$_{121-127}$. For example, a homologous substitute comprises at least one amino acid capable of fulfilling at least one element loss in the epitope. For another example, a mutation procedure is applied in at least one element in the epitope.

bound to IFN$_r$ 1-131 in a dose dependent manner but not to EE-IFN$_r$• represented as the mean optical density (OD) at 405 nm.

FIG. 2*b* demonstrates a Western blot analysis showing the binding of blood plasma from Anti-IFN$_r$□AutoAbs patients (n=4, P1-4) and healthy controls (n=2, C1-2) to IFN$_r$1-131 and EE-IFN$_r$. Plasma from 3 healthy donors had no response to either IFN$_r$1-131 or EE-IFN$_r$.

FIGS. 2*c*-2*e* demonstrate PBMCs from healthy controls that were pre-incubated with 20% Ctrl plasma (n=6) or anti-IFN$_r$ AutoAbs patients' plasma (n=6) and treated with WT IFN$_r$, IFN$_r$_1-131 or EE-IFN$_r$□□ After being gated on the CD14$^+$, p-STAT-1 levels were determined by flow cytometry with the p-STAT-1 monoclonal antibody. Representative histograms (FIG. 2*c*(1)-FIG. 2*c*(2)) and MFI (median fluorescence intensity) (FIG. 2*d*) are shown.

FIG. 2*e* demonstrates that PBMCs from healthy controls were pre-incubated with 20% Ctrl plasma (n=4) or anti-IFN$_r$ AutoAbs patients' blood plasma (n=9) and stimulated with BCG BCG plus WT IFN$_r$, BCG plus IFN$_r$_1431 or BCG plus EE-IFN$_r$••IL12p40 levels in the supernatant were measured by ELISA.

Table 2 demonstrates homologies in hIFN$_r$• peptides $P_{125-133}$ to *Aspergillus* spp. Noc2 proteins. Amino acid numbers correspond to those of proteins published by The National Center for Biotechnology Information (NCBI). AA is an abbreviation for number of amino acids. And the proteins were sampled from *Homo sapiens* (SEQ NO: 22), *Aspergillus terreus* (SEQ NO: 23), *Aspergillus fumigatus* (SEQ NO: 24), *Aspergillus flavus* (SEQ NO: 25), *Aspergillus nidulans* (SEQ NO: 26), *Aspergillus niger* (SEQ NO: 27), *Cryptococcus neoformans* (SEQ NO: 28), *Mycobacterium intracellulare* (SEQ NO: 29) and *Clostridium* sp. MSTE9 (SEQ NO: 30).

TABLE 2

| Protein | Species | AA | | AA | Positive | Accession code |
|---|---|---|---|---|---|---|
| IFNγ $P_{125-133}$ | *Homo sapiens* | 125 | AAKTGKRKRSQML (SEQ ID NO: 22) | 133 | — | GI:56786138 |
| Ribosome assembly protein Noc2 | *Aspergillus terreus* | 105 | TPKTGKRKRSEQQ (SEQ ID NO: 23) | 113 | 9/9 (100%) | GI:115397505 |
| Ribosome assembly protein Noc2 | *Aspergillus fumigatus* | 100 | TPKITGKRKRSEEQ (SEQ ID NO: 24) | 108 | 8/9 (89%) | GI:159131733 |
| Ribosome assembly protein Noc2 | *Aspergillus flavus* | 102 | TPKTGKRKRTEEQ (SEQ ID NO: 25) | 110 | 8/9 (89%) | GI:238483989 |
| Ribosome assembly protein Noc2 | *Aspergillus nidulans* | 103 | SPKIGKRKRSETQ (SEQ ID NO: 26) | 111 | 8/9 (89%) | GI:67517347 |
| Ribosome assembly protein Noc2 | *Aspergillus niger* | 102 | TPKIGKRKRSDEQ (SEQ ID NO: 27) | 110 | 7/9 (78%) | GI:317025642 |
| Hypothetical protein CNAG_05000 | *Cryptococcus neoformans* | 623 | LGSTGKRKRSSMG (SEQ ID NO: 28) | 631 | 7/9 (78%) | GI:405119493 |
| Hypothetical protein OCO_15660 | *Mycobacterium intracellulare* | 124 | NPAGGKRKRSQ-- (SEQ ID NO: 29) | 132 | 7/9 (78%) | GI:379753578 |
| Diguanylate cyclase | *Clostridium* sp. MSTE9 | 14 | KEQSKKRKRSQMT (SEQ ID NO: 30) | 22 | 6/9 (67%) | GI:496353461 |

FIG. 2*a*(1)-FIG. 2*a*(2) demonstrate the affinity of anti-IFN$_r$ AutoAbs to IFN$_r$_1-131 and EE-IFN$_r$□□ by ELISA. Anti-IFN$_r$•AutoAbs from 5 patients' blood plasma was FIG. 3*a*(1)-FIG. 3*a*(2) demonstrate epitope cross reaction mapping used to determine blood plasma binding affinity of the synthetic peptide to *Aspergillus* Noc2, represented as the mean optical density (OD) at 405 nm; blood plasma sample from IFN$_r$ AutoAbs patients (n=9), Mycobacteria infected patients (n=3) and healthy controls (n=3).

FIG. 3b(1)-FIG. 3b(2) demonstrate inhibition of ELISA, where each plasma sample from IFN$_r$ AutoAbs patients (n=7) was pre-incubated with different concentrations of control peptide or *Aspergillus* Noc2 peptide, then all plasma dilutions were examined by ELISA for reactivity against peptide 6.

Figure 3C:
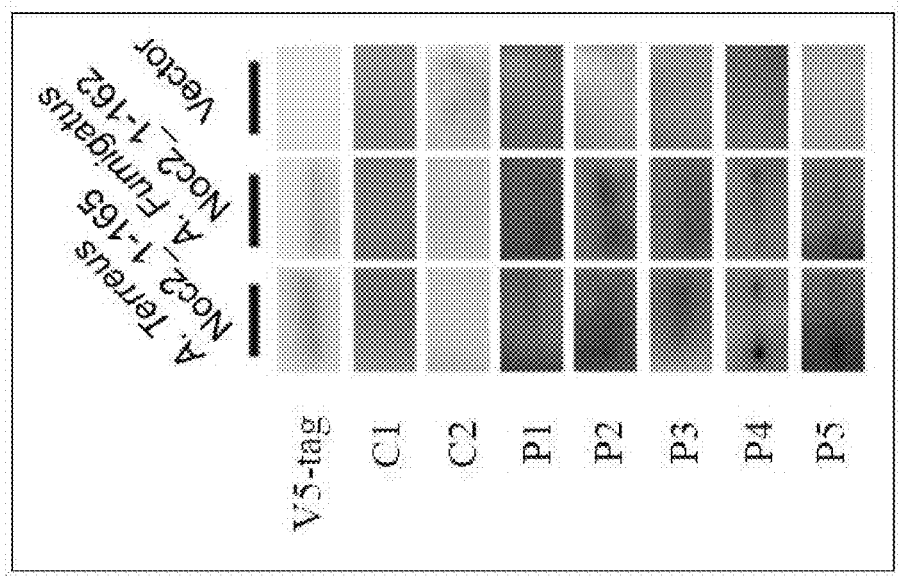
Figure 3E:
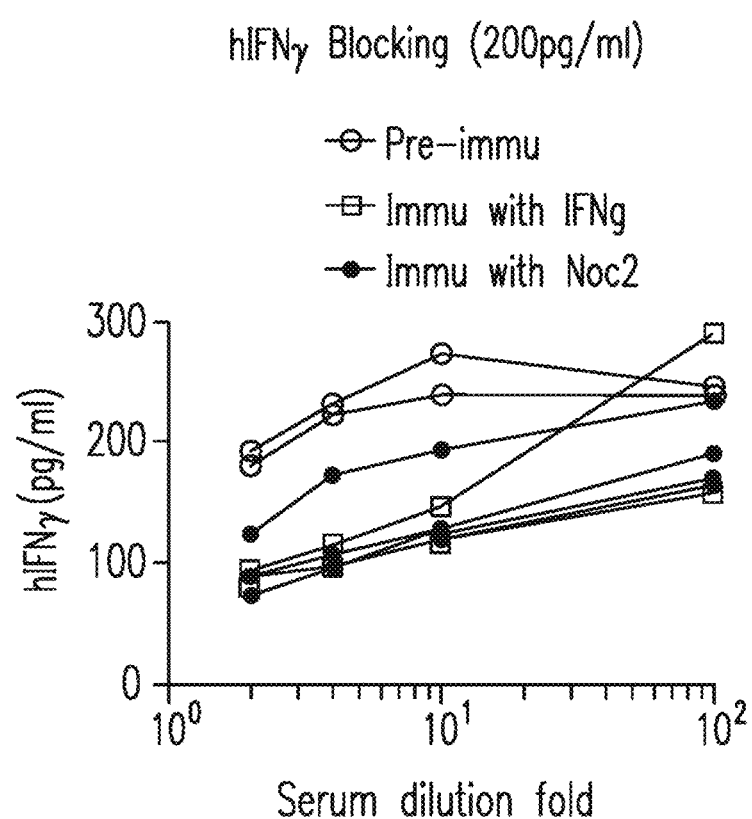

FIG. 3c demonstrates a Western blot analysis showing binding of plasma form Anti-IFN$_r$•AutoAbs patients (n=4, P1-4) and healthy controls (n=2, C1-2) truncated *Aspergillus Terreus* (Amino Acid: 1-165) and *Aspergillus Fumigatus* (Amino Acid: 1-162) recombinant Noc2 protein.

FIG. 3d(1)-FIG. 3d(4) demonstrate immunization with Noc2 peptide induced antibodies to IFN$_r$. Blood sera from pre-immunized rats (n=6), Noc2 peptide-immunized rats (n=4) and Peptide 6-immunized rats (n=2) were mapped to control peptide, Peptide 6 and Noc2 peptide from *Aspergillus terreus* or *Aspergillus fumigatus*. This is represented as the mean optical density (OD) at 405 nm.

FIG. 3*e* demonstrates blood sera from pre-immunized rats (n=2), Noc2 peptide-immunized rats (n=4) and Peptide 6-immunized rats (n=2) were serially diluted and incubated with 200 pg/mL of human $IFN_r$. Sera from pre-immunized rats showed no blocking activities for the detection of $hIFN_r$. However, blood sera from Noc2 peptide-immunized rats (n=4) and Peptide 6-immunized rats (n=2) at dilutions of up to $1/10^2$ inhibited the detection of $hIFN_r$.

FIGS. 3*f*-3*g* demonstrate that THP1 cells were pre-incubated with 50% blood sera from pre-immunized rats (n=2), Noc2 peptide-immunized rats (n=4) or Peptide 6-immunized rats (n=2) and treated with WT $IFN_r$••p-STAT-1 levels were determined by flow cytometry with the p-STAT-1 monoclonal antibody, MFI (median fluorescence intensity) are shown in FIG. 3*f* HLA-DR expression levels were determined by flow cytometry with the HLA-DR monoclonal antibody, and MFI are shown in FIG. 3*g*.

FIGS. 4*a*-4*b* demonstrate that PBMCs from healthy controls (n=5) or anti-$IFN_r$ AutoAbs patients (n=6) were pre-incubated with 20% autologous plasma and treated with WT $IFN_r$, $IFN_r$1-131 or EE-$IFN_r$. After being gated on the $CD14^+$, p-STAT-1 levels were determined by flow cytometry with the p-STAT-1 monoclonal antibody. Representative histograms (FIG. 4*a*(1)-FIG. 4*a*(2)) and MFI (median fluorescence intensity) (FIG. 4*b*) are shown.

FIG. 4*c* demonstrates that PBMCs from healthy controls (n=3) or anti-$IFN_r$ AutoAbs patients (n=6) were pre-incubated with 20% autologous blood plasma and stimulated with BCG BCG plus WT $IFN_r$, BCG plus $IFN_r$_1-131 or BCG plus EE-$IFN_r$••IL12p40 levels in the supernatant were measured by ELISA.

FIGS. 4*d*-4*e* demonstrate that PBMCs from healthy controls (n=5) or anti-$IFN_r$ AutoAbs patients (n=4) were pre-incubated with 20% autologous plasma and treated with WT $IFN_r$, $IFN_r$_1-131 or EE-$IFN_r$. After being gated on the $CD14^+$, HLA-DR expression levels were determined by flow cytometry with the HLA-DR monoclonal antibody. Representative histograms (FIG. 4*d*(1)-FIG. 4*d*(2)) and MFI (median fluorescence intensity) (FIG. 4*e*) are shown.

FIGS. 4*f*-4*g* demonstrate that whole blood from healthy controls (n=4) or anti-$IFN_r$ AutoAbs patients (n=6) was treated with WT $IFN_r$, $IFN_r$_1-131 or EE-$IFN_r$• • After being gated on the $CD14^+$, p-STAT-1 levels were determined by flow cytometry with the p-STAT-1 monoclonal antibody. Representative histograms (FIG. 4*f*(1)-FIG. 4*f*(2)) and MFI (median fluorescence intensity) (FIG. 4*g*) are shown.

FIG. 4*h* demonstrates that whole blood from healthy controls (n=4) or anti-$IFN_r$ AutoAbs patients (n=5) was stimulated with BCG BCG plus WT $IFN_r$, BCG plus $IFN_r$_1-131 or BCG plus EE-$IFN_r$•IL12p40 levels in the supernatant were measured by ELISA.

FIG. 5 demonstrates that direct ELIAS was used to detect AutoAbs against $IFN_r$. Represented as the mean optical density (OD) at 405 nm; blood plasma samples from $IFN_r$ AutoAbs patients (n=2), and healthy controls (n=65) are shown.

FIG. 6*a* demonstrates that IL-12 production levels were measured by ELISA after non-activated, BCG activated or BCG plus $IFN_r$ activated in whole blood from three groups individuals were tested. $IFN_r$ AutoAbs patients (n=3), healthy controls without AutoAbs (n=7), and healthy controls with non-neutralizing $IFN_r$•AutoAbs (n=4) are shown.

FIG. 6*b* demonstrates that $IFN_r$ production levels were measured by ELISA after non-activated, BCG activated or BCG plus IL-12 activated in whole blood from three groups individuals were tested. $IFN_r$ AutoAbs patients (n=3), healthy controls without AutoAbs (n=7), and healthy controls with non-neutralizing $IFN_r$•AutoAbs (n=4) are shown.

FIG. 7 demonstrates epitope mapping used to determine plasma binding affinity of the synthetic peptide to $IFN_r$, represented as the mean optical density (OD) at 405 nm including plasma samples from $IFN_r$ AutoAbs patients (n=3, P1-3), healthy controls without AutoAbs (n=2, C1-2), and healthy controls with non-neutralizing $IFN_r$•AutoAbs (n=5, N1-5).

FIG. 8 demonstrates a Western blot analysis showing the expression of different forms of recombinant $IFN_r$ by a V5-tag antibody.

FIG. 9 demonstrates blood plasma sampled from $IFN_r$•AutoAbs patients (n=5, P1-5) and healthy controls (n=2, C1-2) were probes for vector, $IFN_r$_1-50, $IFN_r$_1-70, $IFN_r$_68-121, $IFN_r$_1-121, $IFN_r$_1-131, and $IFN_r$_1-139 recombinant proteins.

FIG. 10 demonstrates protein mapping used to determine blood plasma binding affinity of the recombinant proteins to $IFN_r$, represented as the mean optical density (OD) at 405 nm including blood plasma samples from healthy controls without AutoAbs (n=3, C1-3), and healthy controls with non-neutralizing $IFN_r$•AutoAbs (n=5, N1-5).

FIGS. 11*a*-11*b* demonstrate that seven patients' blood plasma was serially diluted and incubated with 200 pg/mL of human $IFN_r$ ($hIFN_r$) or murine $IFN_r$ ($mIFN_r$). The blood plasma from healthy donors showed no blocking activities for the detection of $hIFN_r$ or $mIFN_r$. However, plasma from patients with AutoAbs against $IFN_r$ at dilutions of up to $1/10^4$ inhibited the detection of $hIFN_r$ but showed no blocking activity for the detection of $mIFN_r$.

FIG. 12 demonstrates a Western blot analysis showing the expression of different forms of recombinant Noc2 by V5-tag antibody.

FIGS. 13*a*-13*b* demonstrate that THP1 cells were pre-incubated with 50% Sera from pre-immunized rats (n=2), Noc2 peptide-immunized rats (n=4) or Peptide 6-immunized rats (n=2) and treated with WT IFNγ p-STAT-1, and levels were determined by flow cytometry with the p-STAT-1 monoclonal antibody, wherein representative histograms (FIG. 13*a*(1)-FIG. 13*a*(2)) are shown. HLA-DR expression levels were determined by flow cytometry with the HLA-DR monoclonal antibody, wherein representative histograms (FIG. 13*b*(1)-FIG. 13*b*(2)) are shown.

[Embodiment I] Anti-$IFN_r$ Autoantibodies Recognize a C-Terminal Region in $IFN_r$ Peptide•

The inventor tried to identify the epitope recognized by anti-$IFN_r$ AutoAbs isolated from patients by peptide scan:

Six 30-mer peptides, overlapping by a 7 or 8 amino acids and covering the entire coding sequence of human IFN$_r$, were synthesized, and the amino acids sequences of peptides addressing SEQ NOS: 2 to 7 were listed (FIG. 1a). Epitope mapping assay was performed using plasma from three different patient groups: anti-IFN$_r$ AutoAbs patients with disseminated mycobacterial infections (n=15, group-1), patients with mycobacterial infections without anti-IFN$_r$ AutoAbs (n=2, group-2), and healthy controls (n=6, group-3). It was found that only peptide 6 was recognized in the blood plasma isolated from the 12 patients in group-1 (FIG. 1b(1)-FIG. 1b(6)). In contrast, no binding activity to these six peptides was observed in other two patient groups and this observation suggests that recognition of the peptide 6 was not due to a cross-reaction of anti-mycobacterial antibodies. Next, competition ELISA was used to confirm the specificity of the anti-IFN$_r$ AutoAbs to the peptide 6. Blood plasma from group-1 patients was pre-incubated with peptide 6, which led to competition for the binding with coated peptide 6 in a dose dependent manner, and no competition was observed when the control peptides (peptide 1-5) were used as competitors (FIG. 1c(1)-FIG. 1c(2)). These data suggest that the anti-IFN$_r$ AutoAbs from group-1 patients was recognized by one major region in the peptide 6 ($P_{114-143}$).

Figure 5:
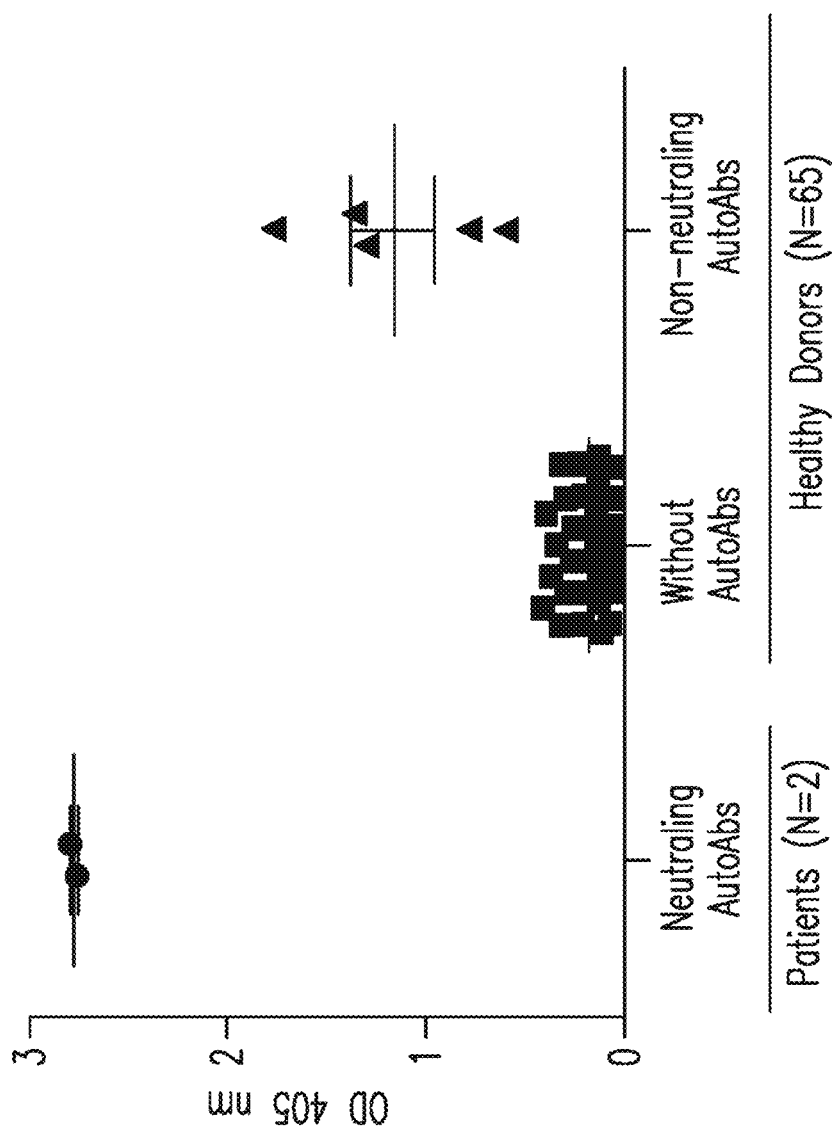
Figure 6A:
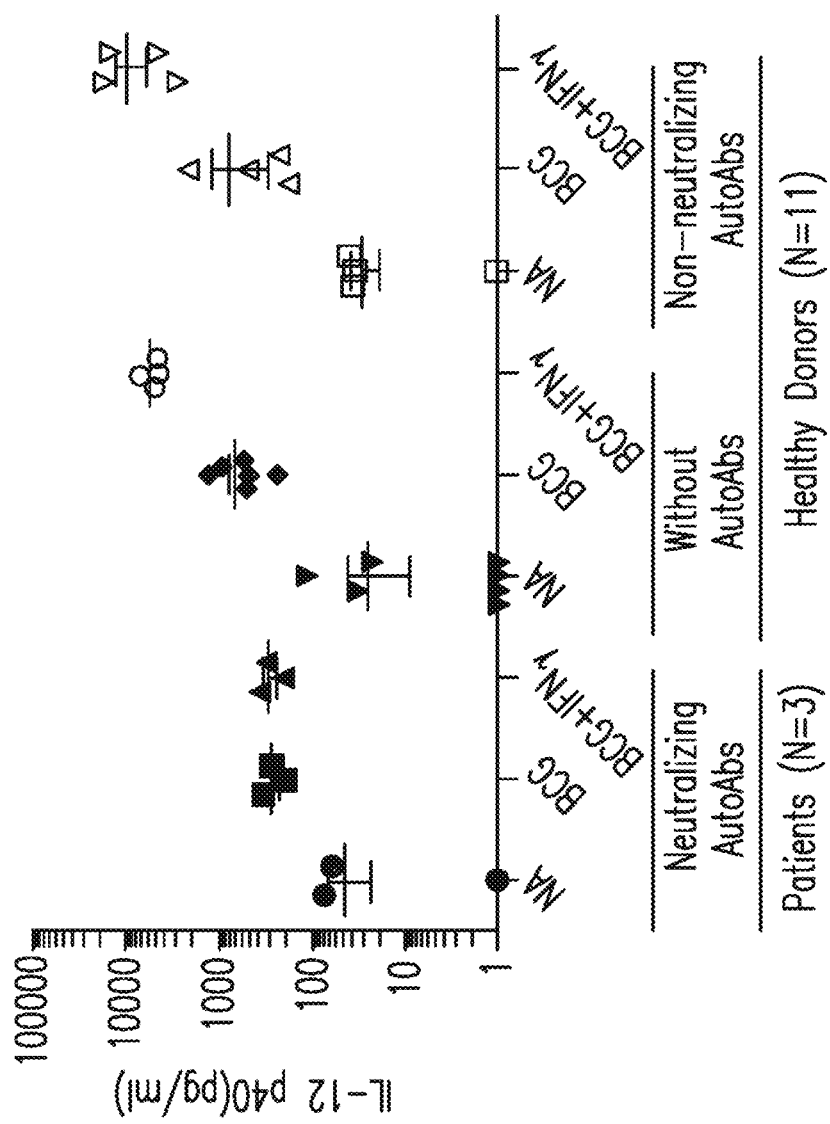
Figure 6B:
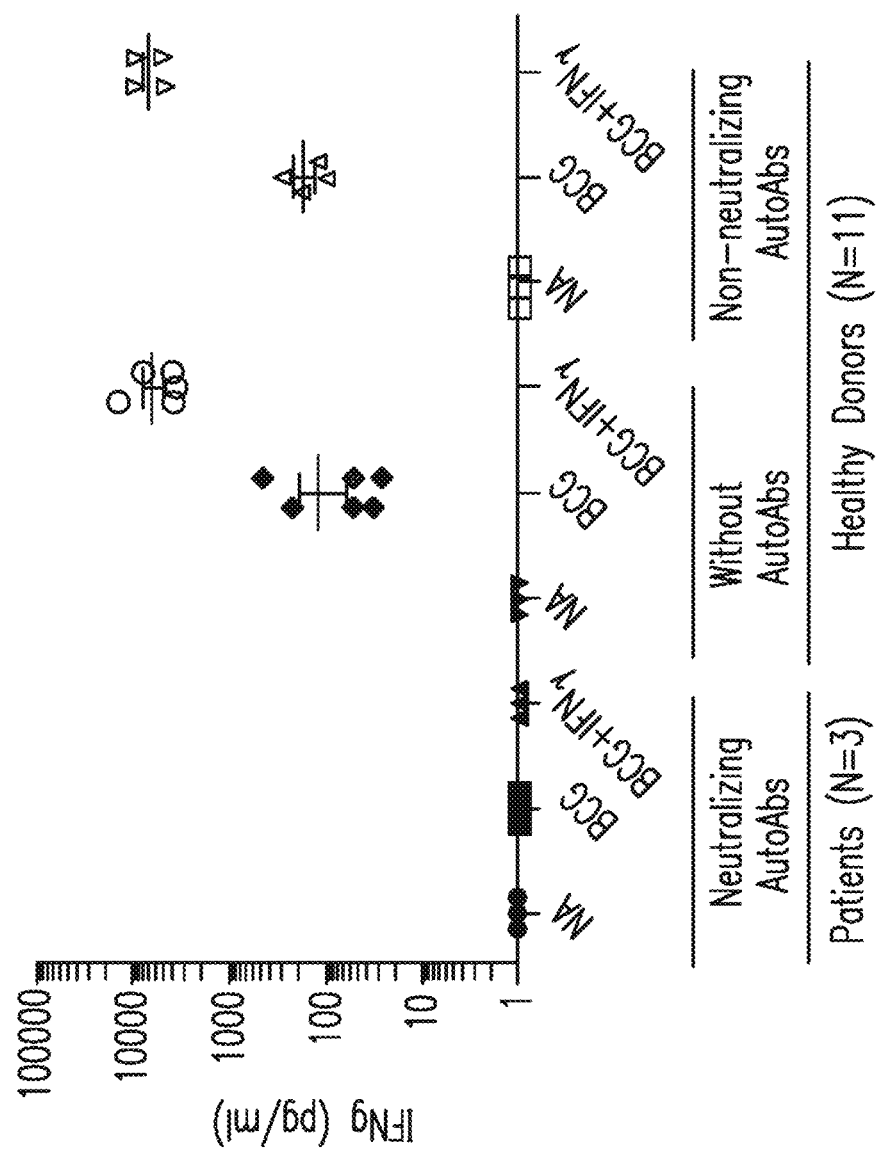
Figure 7:
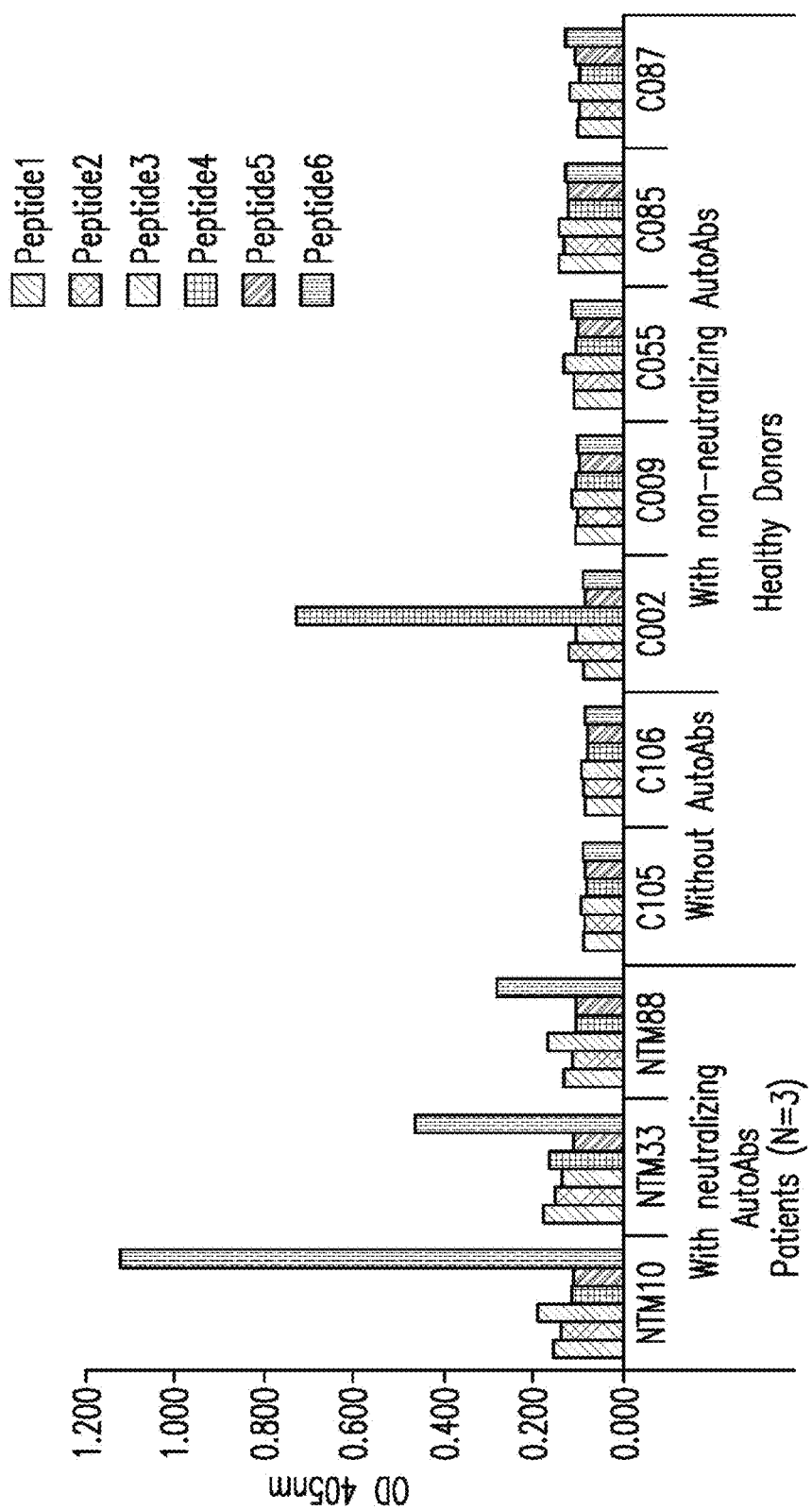
Figure 8:
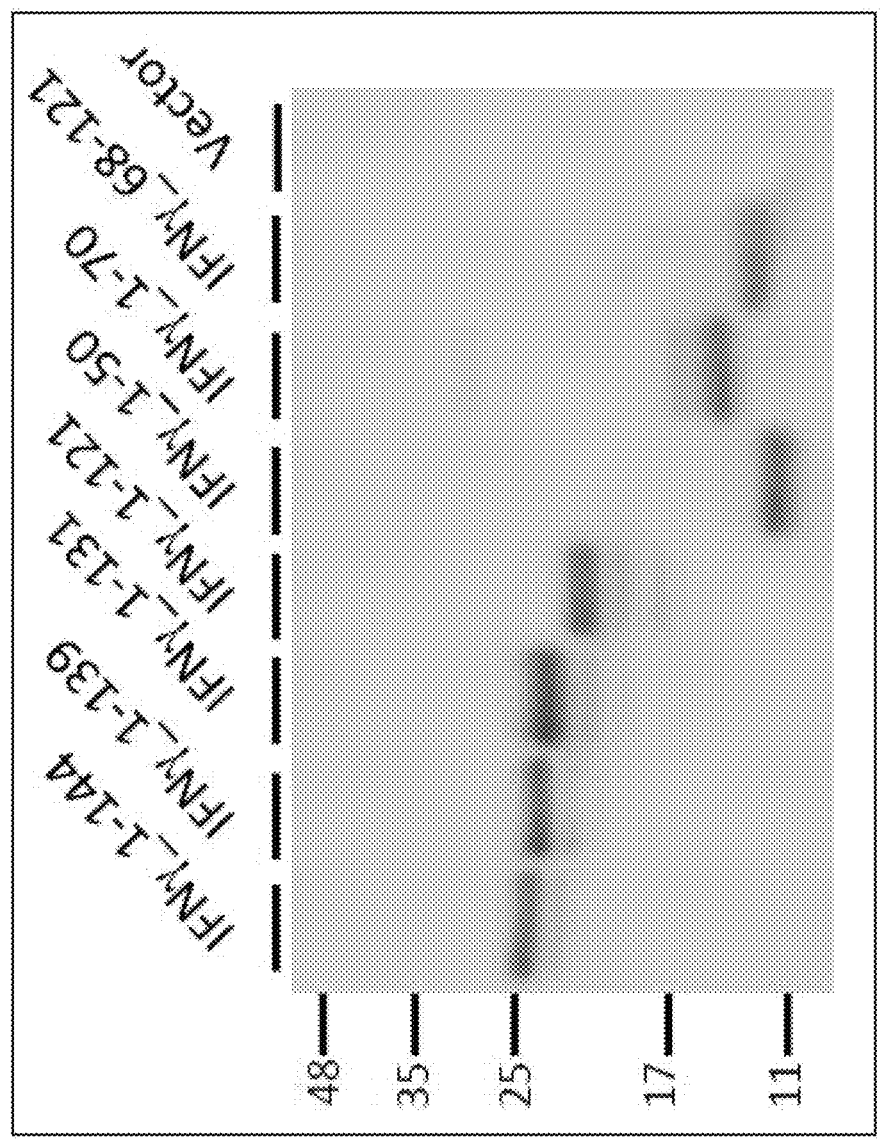

In contrast to neutralizing AutoAbs to IFN$_r$• in patients with mycobacterial infections, non-neutralizing AutoAbs against IFN$_r$ had been reported in healthy individuals. Five donors were found with AutoAbs against IFN$_r$ out of 65 healthy controls by ELISA (FIG. 5). AutoAbs from these five healthy individuals showed a non-neutralizing effect on IFN$_r$ in terms of induction of IL-12 production. In contrast to neutralizing IFN$_r$•AutoAbs from patients, non-neutralizing AutoAbs from healthy donors did not recognize peptide 6 (FIG. 8). These data indicate that the IFNγ AutoAbs from patients with disseminated mycobacterial infections, but not non-neutralizing IFNγ AutoAbs, recognized a major region on peptide 6.

[Embodiment II] Predictions of B-Cell Epitopes Using Computer Modeling

For further confirmation of the precise region recognized by anti-IFN$_r$ AutoAbs, the inventor scanned the primary sequence of IFN$_r$ for possible B-cell linear epitopes and possible surface acceptability in silico. It was found several candidate epitopes addressing SEQ NO: 8-14 in the full length IFN$_r$•(FIG. 1d). Considering the higher prediction scores for screening features and located in the peptide 6, the epitope $P_{121-131}$ SPAAKTGKRKR (SEQ ID NO: 33) was predicted in B-cell epitope prediction algorithms and $P_{126-131}$ TGKRKR (SEQ ID NO: 37) was predicted in Surface Acceptability prediction algorithms. These results were consistent with peptide epitope mapping data. The critical epitope $P_{121-131}$ SPAAKTGKRKR (SEQ ID NO: 33) that we identified is located on an unfolded sequence in the C-terminal region. It extends into the solvent and does not strongly interact with the remainder of the molecules (FIG. 1e).

Figure 9:
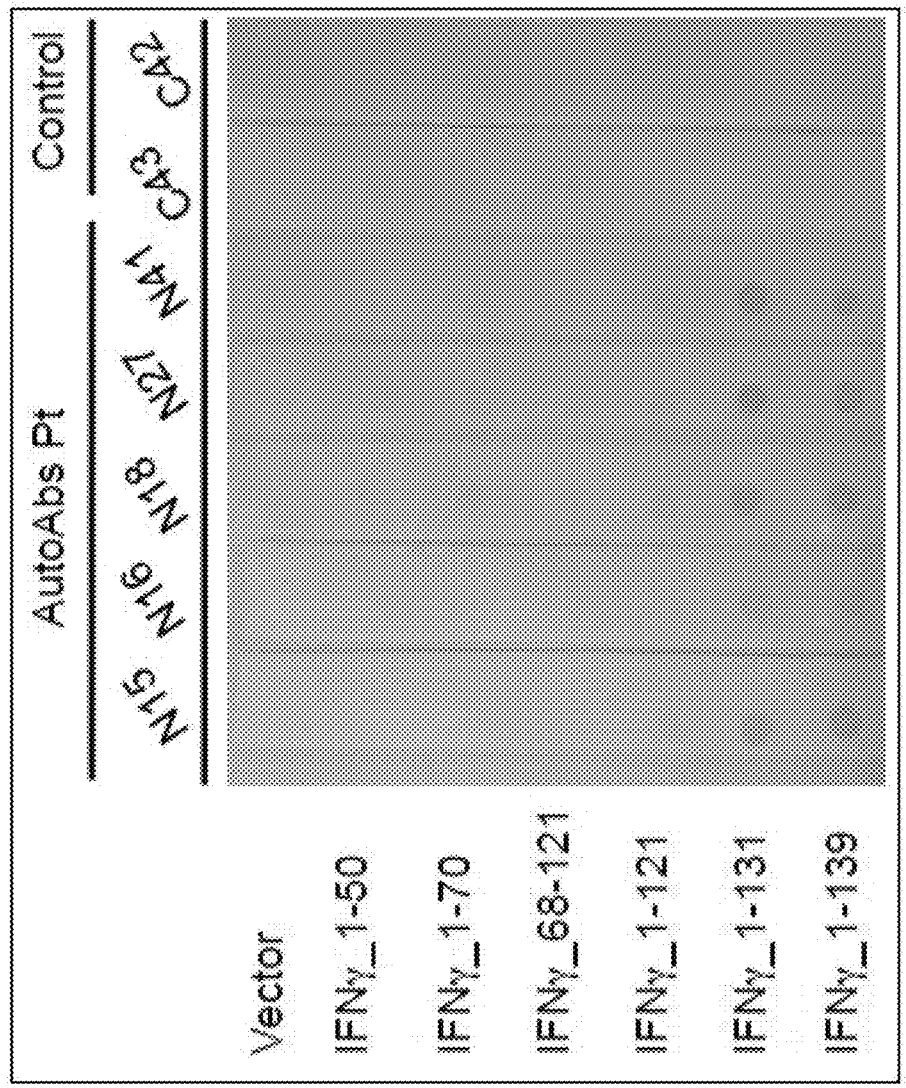
Figure 10:
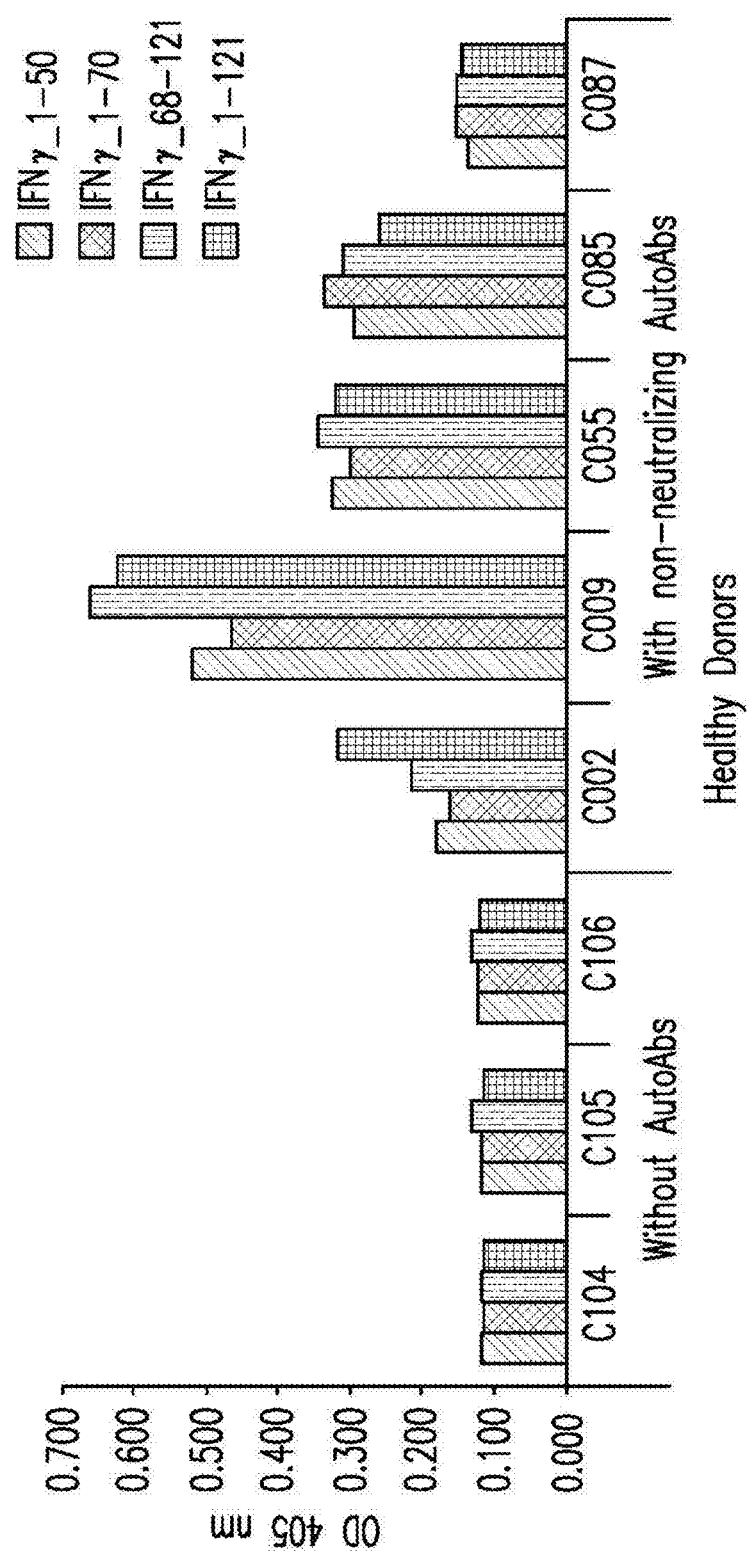
Figure 11A:
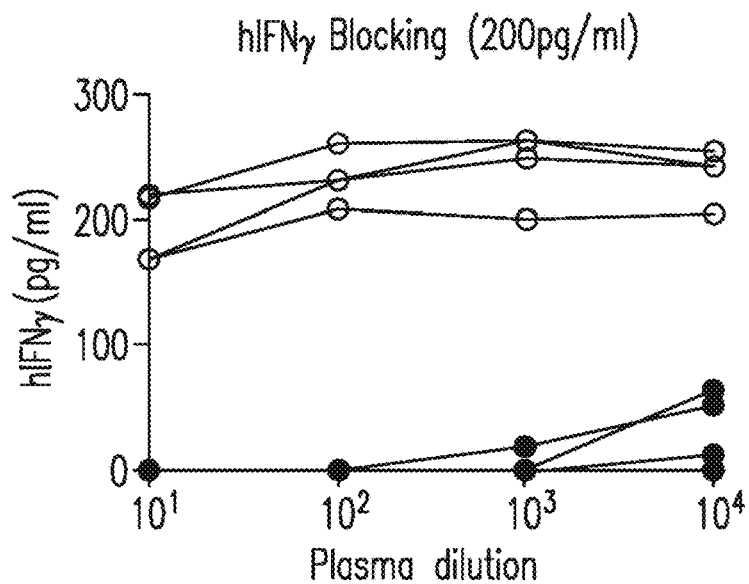
Figure 11B:
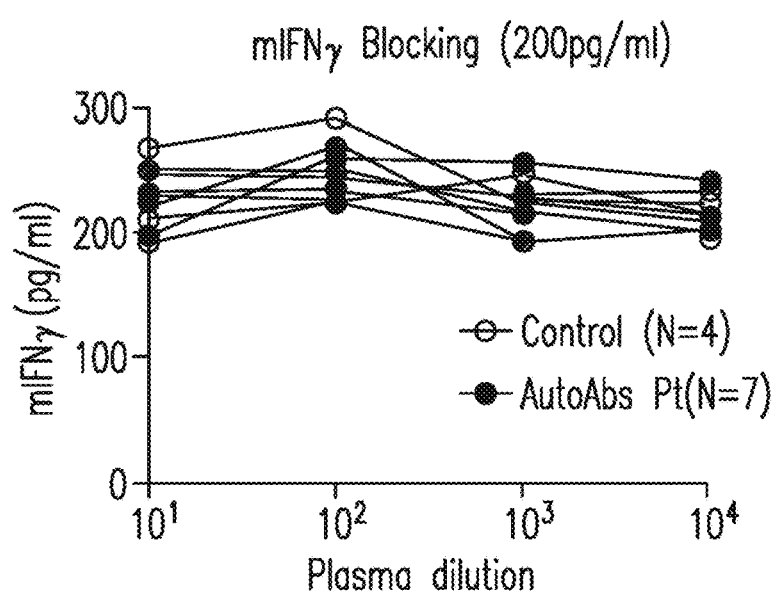

[Embodiment III] Anti-IFN$_r$ Autoantibodies Recognize a C-Terminal Region in IFN$_r$• Protein In order to investigate whether anti-IFN$_r$ AutoAbs from group-1 patients recognized the same region in the native IFN$_r$ protein, we generated various truncated IFN$_r$ by Schneider 2 cell expression system (FIG. 1f and FIG. 9). It was found that only full-length IFN$_r$ (IFN$_r$ 1-144) and deletion clone IFN$_r$ 1-131 were recognized by blood plasma isolated from the group-1 patients (FIG. 1g(1)-FIG. 1g(6)). In contrast, blood plasma isolated from the group-2 and group-3 patients did not recognize all the recombinant IFN$_r$ tested. In Western blot and dot blot assays, we also observed similar phenomena that only full-length IFN$_r$ 1-144 (data not shown) and deletion clone IFN$_r$ 1-139 and IFN$_r$ 1-131 were recognized by anti-IFN$_r$ AutoAbs, but not other truncates IFN$_r$•(FIGS. 1h and 10). These data suggest that a major anti-IFN$_r$□AutoAbs-recognized B-cell epitope, $P_{121-131}$ (SPAAKTGKRKR) (SEQ NO: 33) was located at the C-terminal of IFN$_r$.

[Embodiment IV] EE-IFNγ

Inside the epitope region we identified, a.a. 128-131 (KRKR) (SEQ ID NO: 38) (the last 4 resides in SEQ NO: 20) is crucial for the bioactivity of IFN$_r$□ and conserved in most species.

Nevertheless, a.a. 121-127 is less conserved among different species (human: SPAAKTG (SEQ ID NO: 39) (the $6^{th}$-$12^{th}$ resides in SEQ NO: 20); murine: LPESSLR (SEQ NO: 1)) (Table 1).

Figure 12:
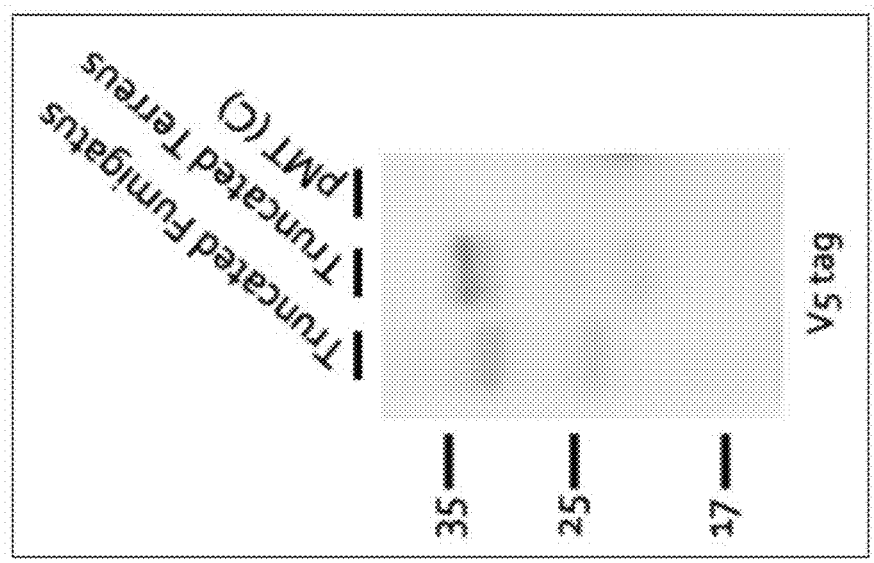

It had been observed that blood plasma from randomly selected patients with anti-IFN$_r$ AutoAbs did not show blocking activity on the murine IFN$_r$ (FIG. 12), which suggests that SPAAKTG (the $6^{th}$-$12^{th}$ resides in SEQ NO: 20) is a necessary component for the binding of anti-IFN$_r$ AutoAbs. Previous studies demonstrated that the precise sequence in a.a. 121-127 was not critical for IFN$_r$ functions, and the deletion of some amino acids from the C-terminal of human IFN$_r$ resulted in increasing bioactivity.

Following these observations, the inventor generated an EE-IFN$_r$ protein by substituting the human $P_{121-127}$ SPAAKTG sequence (SEQ ID NO: 39) (the $6^{th}$-$12^{th}$ resides in SEQ NO: 20) with murine LPESSLR sequence (SEQ NO: 1) in the IFN$_r$ 1-131 protein (Table 1).

In other embodiments, EE-IFNγ may be further combined with pharmaceutically acceptable excipients or carriers for clinical use.

The excipient in the present invention also refers to a pharmaceutically acceptable carrier or excipient, or a bio-available carrier or excipient, including a solvent, dispersant, coating, antibacterial or antifungal agent, preservative or slow absorber, which is a proper compound used to prepare a formulation in the prior art. Usually such a carrier or excipient does not have any activity for treatments itself. And the compound disclosed in the present invention cooperating with a pharmaceutically acceptable carrier or excipient is prepared as various formulations, and will not result in adverse drug reactions, allergies or other inappropriate responses after it is administered to animals or humans. Thus the compound in the present invention, cooperating with a pharmaceutically acceptable carrier or excipient, can be used in clinics and humans.

"Effective dose" means a dose which is enough to improve or prevent medical symptoms or biological manifestation. The effective dose may be also stated as a casting dose for use in diagnosis. Unless there is another description in the specification, "active compound" and "pharmaceutically active compound" are substitutes for each other and refer to a pharmaceutical, pharmacological or therapeutic substance as well as other effective material.

Using ELISA, we observed that the affinity of anti-IFN$_r$ AutoAbs to EE-IFN$_r$ was markedly decreased in comparison with wild type (WT) IFN$_r$ 1-131 (FIG. 2a(1)-FIG. 2a(2)).

Figure 2B:
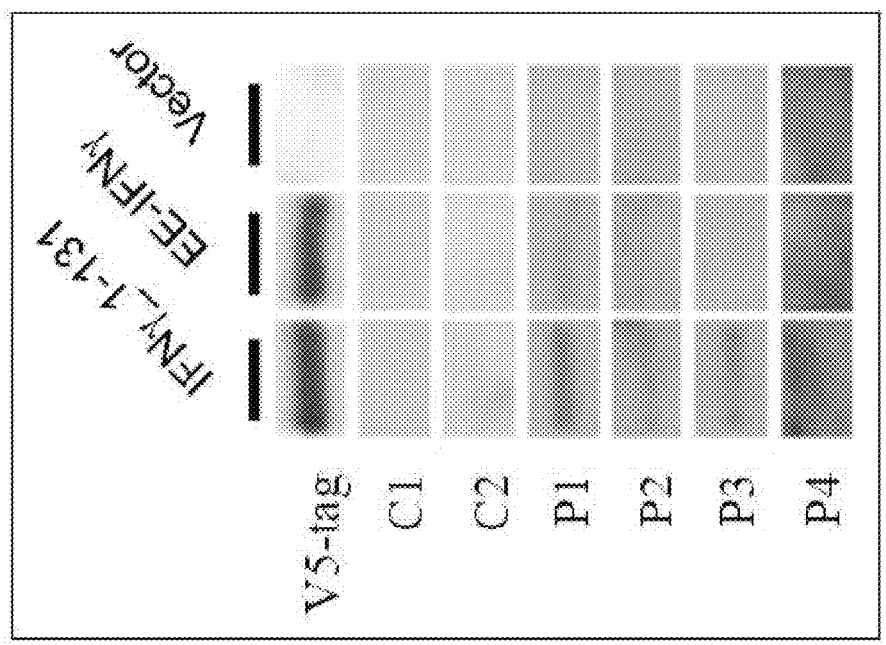

With the aid of Western blot, again, we observed a similar different affinity to anti-IFN$_r$ AutoAbs between EE-IFN$_r$ and WT IFN$_r$ 1-131 (FIG. 2b). These data suggest that the epitope of anti-IFN$_r$ AutoAbs is located in a.a. 121-131 and SPAAKTG was a necessary component for recognition.

Figure 3F:
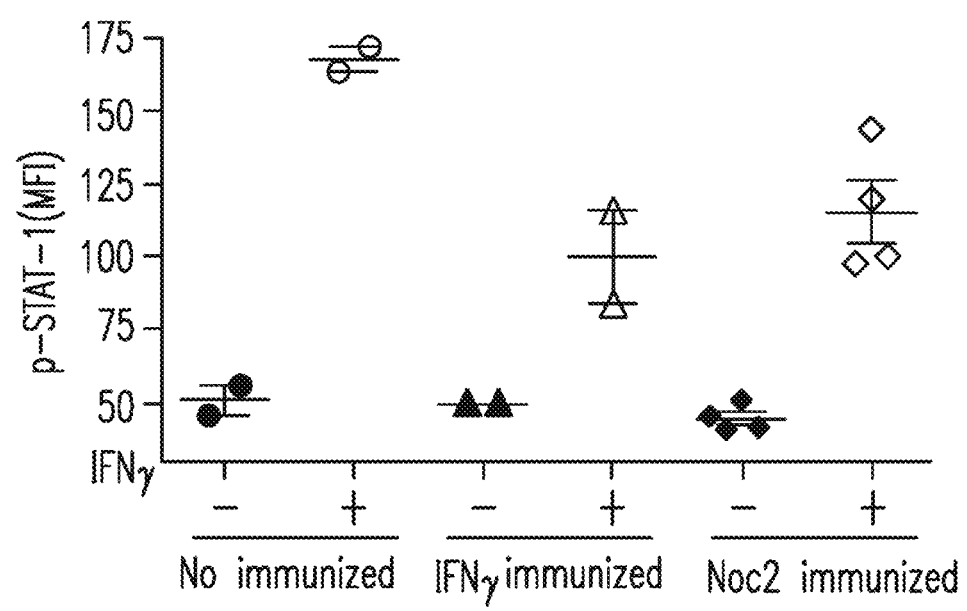
Figure 3G:
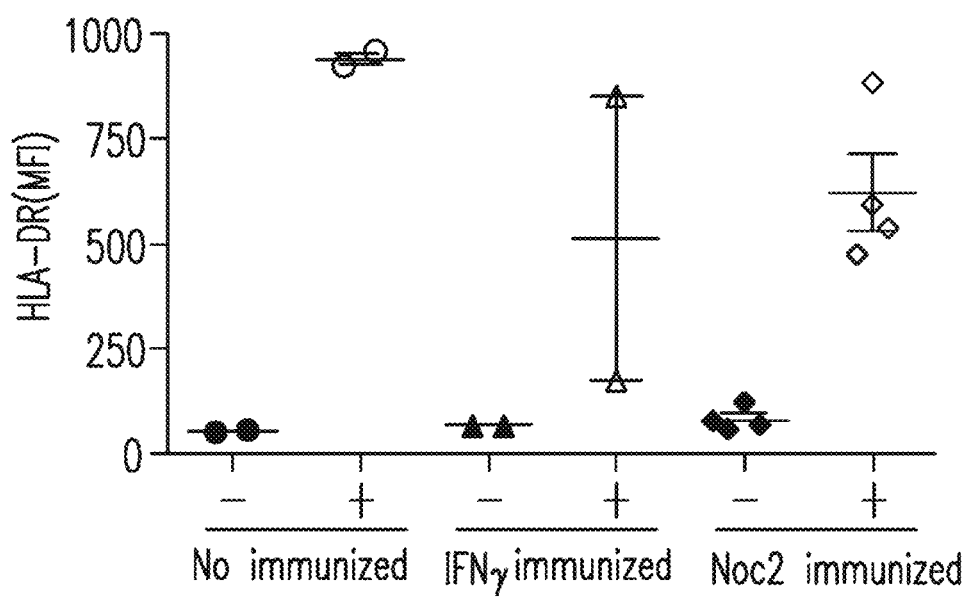

[Embodiment V] Anti-IFN$_r$ AutoAbs to Epitope P$_{121-131}$ have Neutralizing Activity on IFN$_r$ The inventor aimed to know if anti-IFN$_r$ AutoAbs to epitope P$_{121-131}$ played a critical role in the neutralizing effect in an anti-IFN$_r$ AutoAbs disease. A previous study showed that substitution of the homologous murine sequence between residue 121 and residue 127 resulted in only a small decrease in biological activity. The biological activity of EE-IFN$_r$ was tested by measuring the phosphorylation of signal transducers and activators of transcription 1 (p-STAT1) signaling assay by flow cytometry and interleukin-12 (IL-12) production through ELISA. Up-regulation of the p-STAT1 signaling was observed in the controls' peripheral blood mononuclear cells (PBMCs) that were activated with recombinant IFN$_r$, WT IFN$_r$ 1-131, or E (FIG. 3f). Similar results were also be observed in an HLA-DR expression assay (FIG. 3g). These data indicate that antibodies to *Aspergillus* Noc2 not only bind to human IFN$_r$, but also inhibit IFN$_r$ downstream signaling. Thus, rats immunized with Noc2 had a break in the immunological tolerance to IFN$_r$ and anti-IFN$_r$ antibodies were evoked through the process of molecular mimicry.

[Embodiment X] EE-IFN$_r$ Application in Anti-IFN$_r$ AutoAbs Therapy Ex Vivo

Figure 2D:
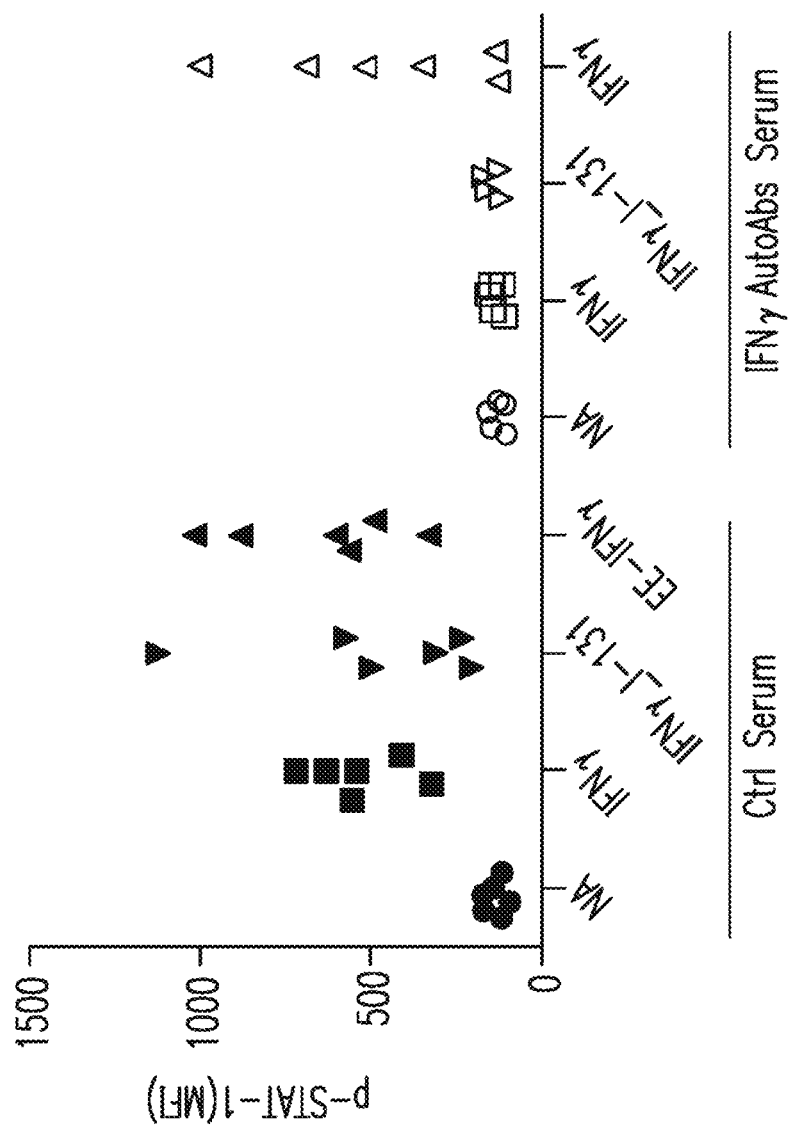
Figure 2E:
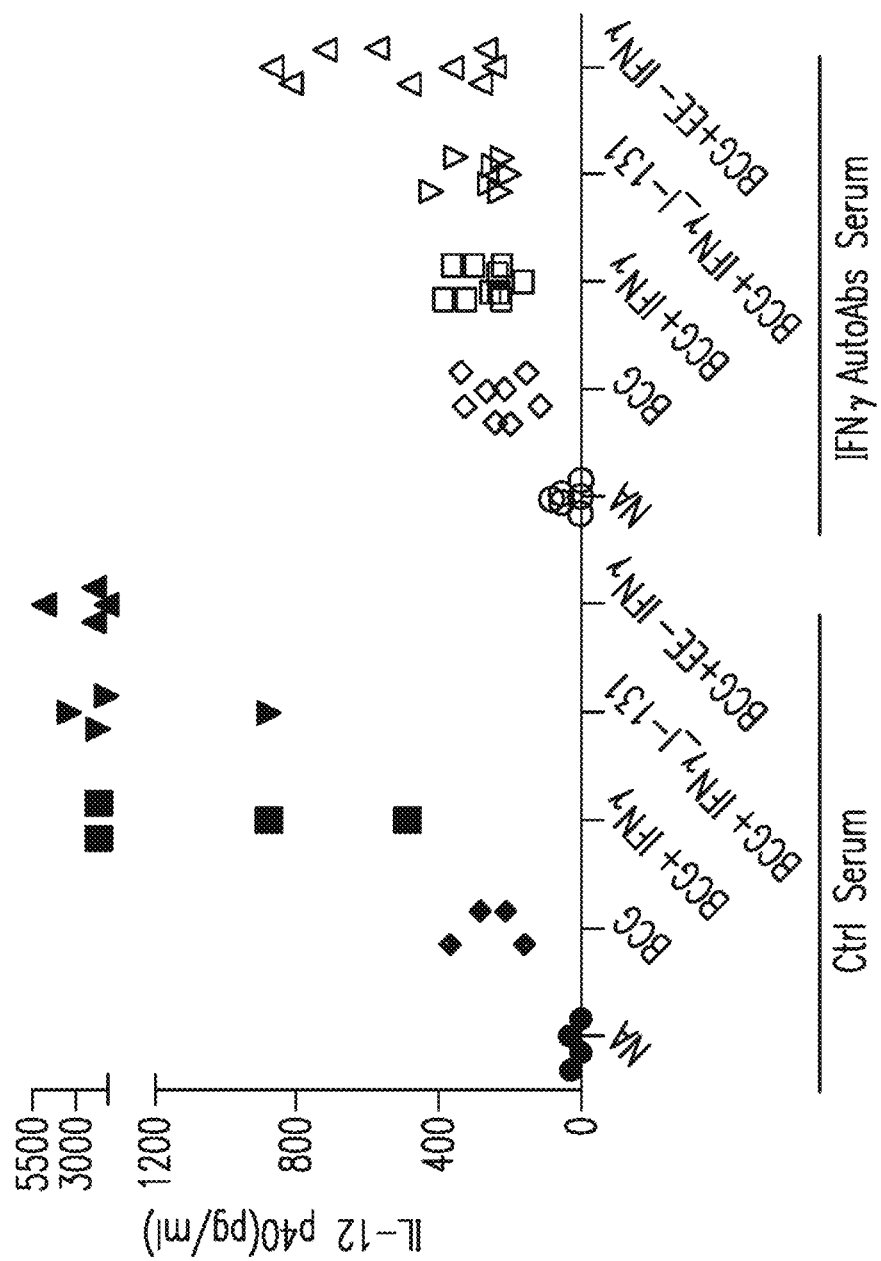
Figure 4B:
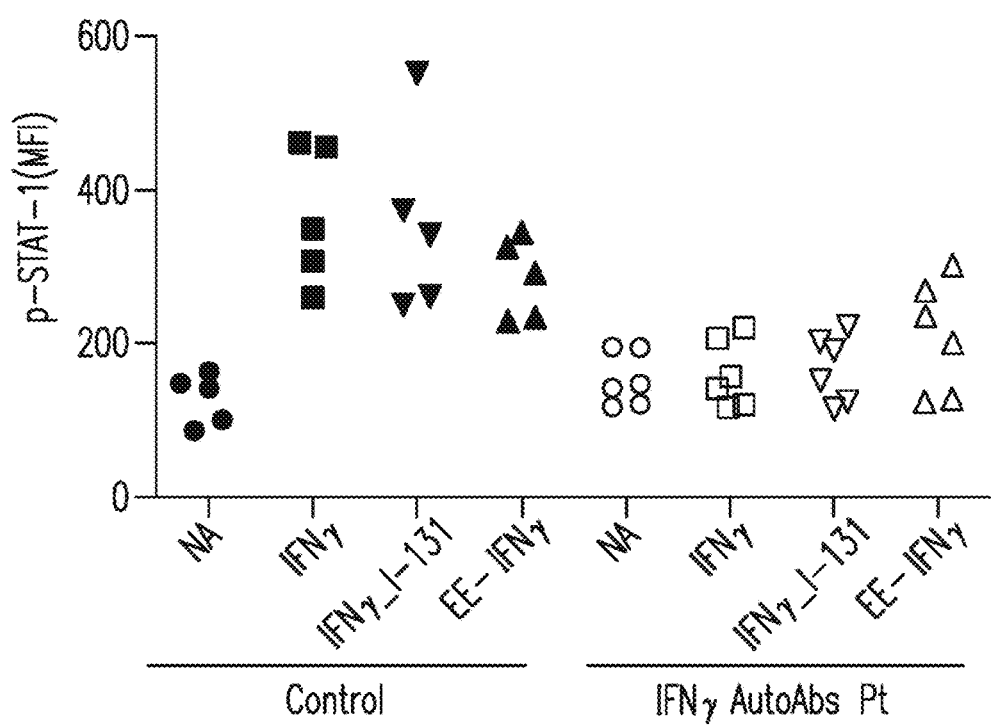
Figure 4C:
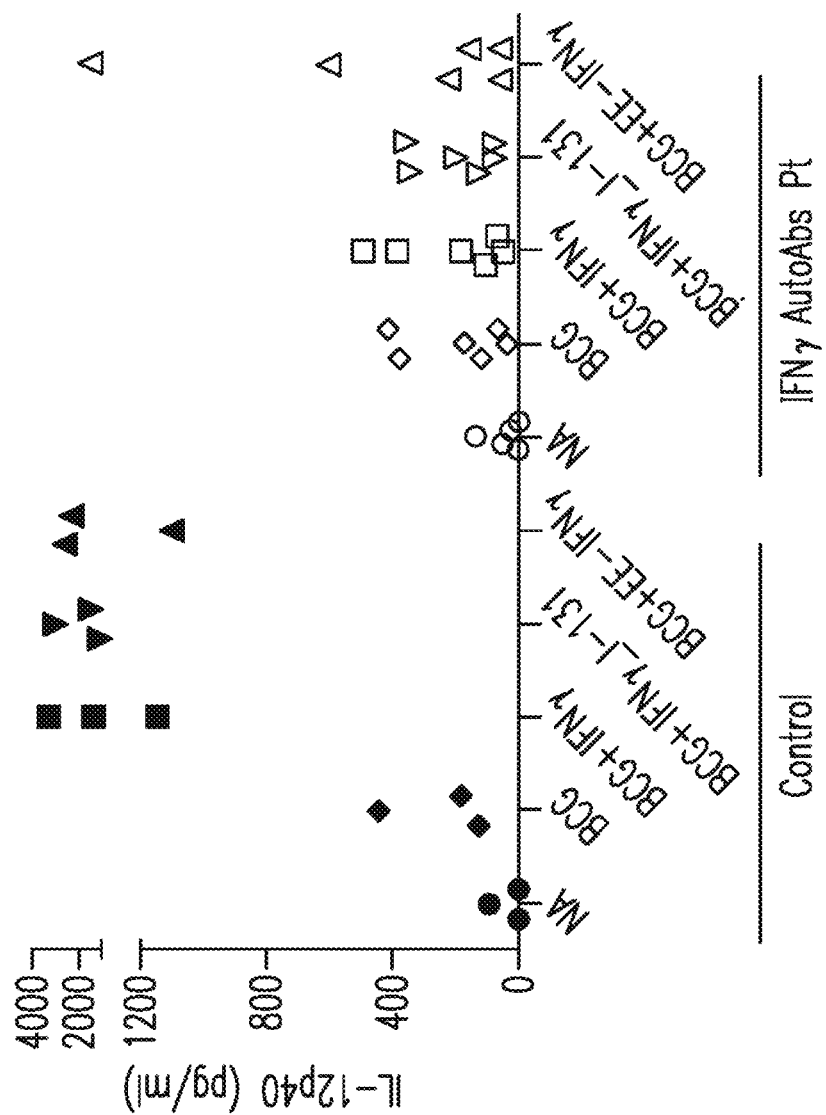
Figure 4E:
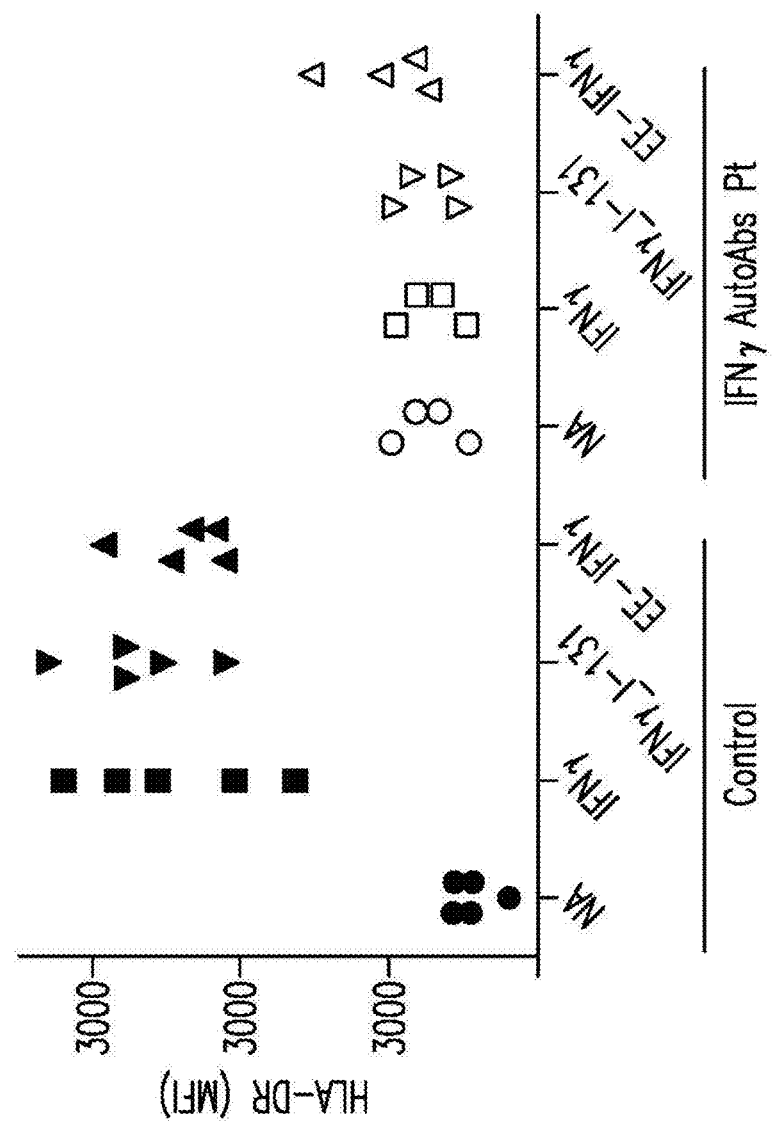

The inventor showed that EE-IFN$_r$ could restore IFN$_r$ activated STAT-1 signaling and promote IL-12/HLA-DR expression in control PBMCs/THP1 cells with the presence of anti-IFN$_r$ AutoAbs (FIGS. 2d-2f). Consequently, we investigated the possibility of using EE-IFN$_r$ to restore the IFN$_r$ function in patients with anti-IFN$_r$ AutoAbs ex vivo. Patients' PBMCs were pre-incubated with 10% autologous blood plasma and stimulated with EE-IFN$_r$ or BCG plus EE-IFN$_r$ to measure p-STAT1 signaling or IL-12 production. It was observed that up-regulated p-STAT1 signaling cannot be observed when IFN$_r$ AutoAbs patients' PBMCs are pre-incubated with 10% autologous blood plasma and stimulated with recombinant IFN$_r$ and WT IFN$_r$ 1-131. In contrast, EE-IFN$_r$ could restore p-STAT1 signaling in four of six IFN$_r$ AutoAbs patients' PBMCs pre-incubated with 10% autologous blood plasma (FIGS. 4a-4b). Moreover, BCG plus EE-IFN$_r$ could restore IL-12p40 production in three of six IFN$_r$ AutoAbs patients' PBMCs pre-incubated with 10% autologous blood plasma in contrast to BCG plus recombinant IFN$_r$ or plus WT IFN$_r$ 1-131 (FIG. 4c). The similar phenomena was also be observed in an HLA-DR expression assay. It was found that up-regulated HLA-DR expression levels were not observed when IFN$_r$ AutoAbs patients' PBMCs was pre-incubated with 10% autologous blood plasma and stimulated with recombinant IFN$_r$ and WT IFN$_r$ 1-131. In contrast, EE-IFN$_r$ could restore the HLA-DR expression levels in four of six IFN$_r$ AutoAbs patients' PBMCs that were pre-incubated with 10% autologous plasma (FIGS. 4d-4e).

Figure 4G:
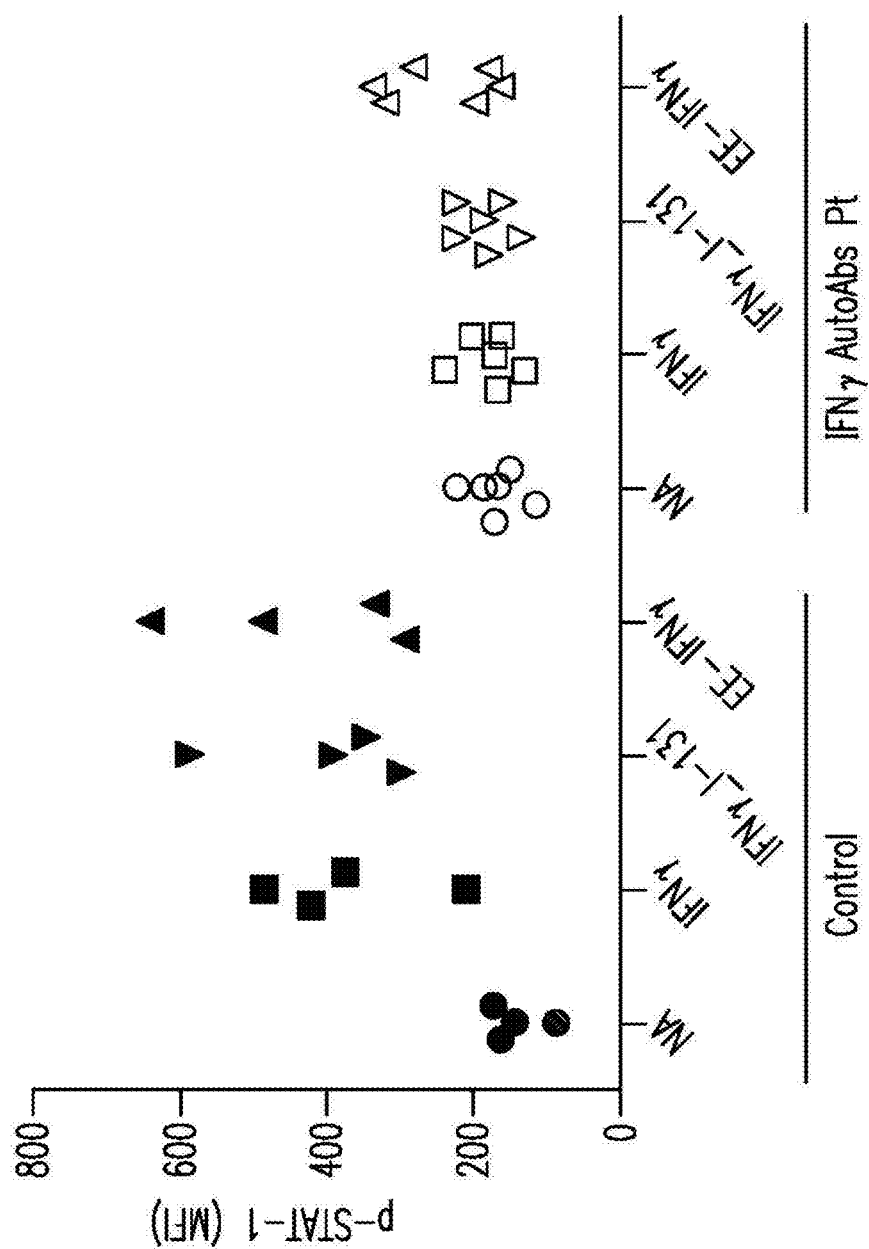
Figure 4H:
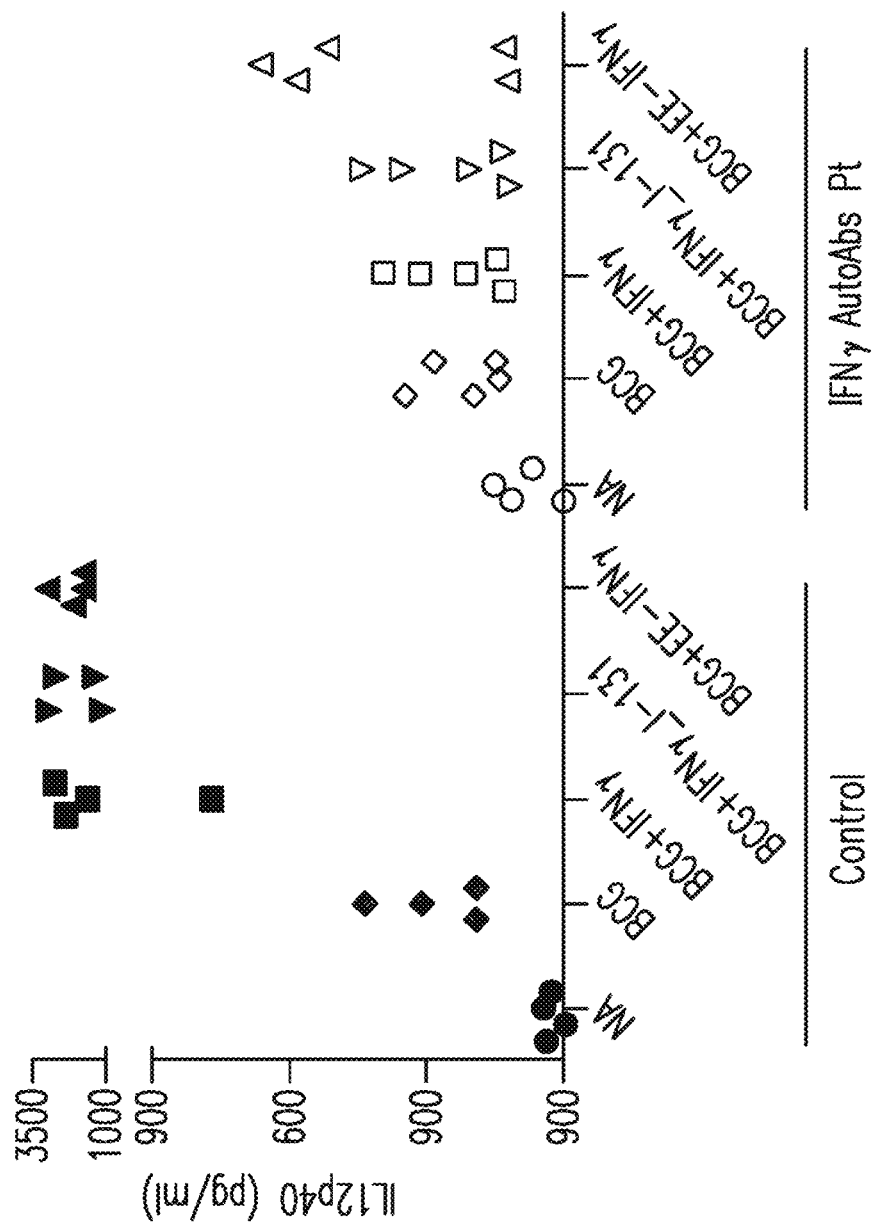

Next, the inventor examined EE-IFN$_r$ bioactivity to restore IFN$_r$ receptor activation in IFN$_r$ AutoAbs patients' whole blood ex vivo. The p-STAT1 signal was up-regulated in controls' whole blood after being stimulated with recombinant commercial IFN$_r$, WT IFN$_r$ 1-131 or EE-IFN$_r$. The up-regulated p-STAT1 signaling was not found when IFN$_r$ AutoAbs patients' whole blood was stimulated with recombinant IFN$_r$ and WT IFN$_r$ 1-131. In contrast, EE-IFN$_r$ could restore p-STAT1 signaling in four of six IFN$_r$ AutoAbs patients' whole blood (FIGS. 4f-4g). Moreover, BCG plus EE-IFN$_r$ could restore IL-12p40 production in three of six IFN$_r$ AutoAbs patients' whole blood in contrast to BCG plus commercial IFN$_r$ or plus WT IFN$_r$ 1-131R (FIG. 4h). Taking these data together, EE-IFN$_r$ could restore bioactivity not only in IFN$_r$ AutoAbs patients' autologous plasma but also in their whole blood ex vivo.

In conclusion, the inventor identified a major epitope in the C-terminal of IFN$_r$ recognized by anti-IFN$_r$ AutoAbs, and these AutoAbs could cross-react with *Aspergillus* Noc2 protein. The inventor hypothesizes that in the presence of specific HLA class II alleles, neutralizing anti-IFN$_r$ AutoAbs, which recognized a limited epitope P$_{121-131}$ in the C-terminal of IFN$_r$, were triggered by Noc2 protein through the mechanism of molecular mimicry. Moreover, the inventor generated a potential therapeutic EE-IFN$_r$, which could restore the IFN$_r$ signaling pathway in the presence of patients' blood samples ex vivo. These data suggest that the anti-IFN$_r$ AutoAbs to P$_{121-131}$ is the one or the only crucial AutoAbs which causes this disease. These findings provide a new model for the pathogenesis of disseminated mycobacterial infections caused by anti-IFN$_r$ AutoAbs and a new therapeutic strategy for this devastating disease.

Further Embodiments

1. A method for evaluating an efficacy of an isolated recombinant human interferon gamma (hIFN$_r$) for regulating a peripheral blood mononuclear cell (PBMC), comprising the steps of:
   providing the PBMC from a subject with anti-interferon gamma autoantibodies;
   mixing the isolated recombinant human interferon gamma with the PBMC, wherein the isolated recombinant human interferon gamma contains a homologous substitute; and
   evaluating the efficacy of the isolated recombinant human interferon gamma according to an expression level of a phosphorylation of signal transducers and activators of transcription 1 (p-STAT1) generated by the PBMC.

2. The method as claimed in Embodiment 1, wherein the isolated recombinant human interferon gamma is produced by the following steps:
   determining an epitope of a subject suffering from a disseminated mycobacterial infection, the epitope is chosen from at least one residue in a human interferon gamma; and
   applying a mutation procedure to the at least one residue to activate a receptor of the human interferon gamma which is not neutralized by an autoantibody of the human interferon gamma.

3. The method as claimed in Embodiment 1, wherein the recombinant human interferon gamma is characterized by an epitope of a subject suffering from a disseminated mycobacterial infection; and
   the homologous substitute substitutes for at least one residue in the epitope.

4. The method as claimed in Embodiment 3, wherein the epitope is located between residue 121 and 127 from a C-terminal of a human interferon gamma.

5. The method as claimed in Embodiment 3, wherein the homologous substitute includes a peptide "Leu-Pro-Glu-Ser-Ser-Leu-Arg" (SEQ NO: 1).

6. The method as claimed in Embodiment 3, wherein the recombinant human interferon gamma further includes one of a pharmaceutically acceptable excipient and a pharmaceutically acceptable carrier.

7. The method as claimed in Embodiment 3, wherein the recombinant human interferon gamma up-regulates the expression level of the p-STAT1 demonstrating a bioactivity of a hIFN$_r$.•••

8. A method for evaluating an efficacy of an isolated recombinant cytokine for regulating a peripheral blood mononuclear cell (PBMC), comprising the steps of:
   providing the PBMC from a subject with an anticytokine autoantibody;
   mixing the isolated recombinant cytokine with the PBMC, wherein the isolated recombinant cytokine contains a homologous substitute; and
   evaluating the efficacy of the isolated recombinant cytokine according to an expression level of an interleukin-12 (IL-12) generated by the PBMC.

9. The method as claimed in Embodiment 8, wherein the isolated recombinant human interferon gamma is produced by the following steps:

determining an epitope of a subject suffering from a disseminated mycobacterial infection, wherein the epitope lacks at least one residue in the amino acid sequence; and substituting the homologous substitute for the at least one residue in the epitope.

10. The method as claimed in Embodiment 9, wherein the epitope is located between residue 121 and 127 from a C-terminal of a human interferon gamma.

11. The method as claimed in Embodiment 9, wherein the homologous substitute includes a peptide "Leu-Pro-Glu-Ser-Ser-Leu-Arg" (SEQ NO: 1).

12. A recombinant protein □, comprising:

a human interferon gamma having a sequence replaced by a peptide of "Leu-Pro-Glu-Ser-Ser-Leu-Arg", wherein the recombinant protein is used to activate a receptor of an interferon gamma ($IFN_r$) and is free from neutralization by an autoantibody of the interferon gamma of a subject suffering from a disseminated mycobacterial infection.

13. The recombinant protein as claimed in Embodiment 12, wherein the subject is immunized with a human interferon gamma.

14. The recombinant protein as claimed in Embodiment 12, wherein the subject is immunized with *Aspergillus* Noc2.

15. The recombinant protein as claimed in Embodiment 12, wherein the sequence has a C-terminal and is located between residue 121 and 127 from the C-terminal.

16. The recombinant protein as claimed in Embodiment 15, wherein the recombinant protein is characterized by an expression of a phosphorylation of signal transducers and activators of transcription 1 (p-STAT1).

17. The recombinant protein as claimed in Embodiment 15, wherein the recombinant protein is characterized by an expression of an interleukin-12 (IL-12).

18. The recombinant protein as claimed in Embodiment 15, wherein the recombinant protein is characterized by an expression of Human Leukocyte Antigen-antigen D Related (HLA-DR) expression.

19. The recombinant protein as claimed in Embodiment 15, wherein the recombinant protein further includes one of a pharmaceutically acceptable excipient and a pharmaceutically acceptable carrier.

20. The recombinant protein as claimed in Embodiment 15, wherein the C-terminal of the human interferon gamma is recognized by the autoantibody of the interferon gamma.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A method for evaluating an efficacy of an isolated recombinant human interferon gamma (rhIFNγ) for regulating a peripheral blood mononuclear cell (PBMC), comprising the steps of:

providing the PBMC from a subject with anti-interferon gamma autoantibodies;

mixing the isolated recombinant human interferon gamma (rhIFNγ) with the PBMC, wherein the isolated recombinant human interferon gamma (rhIFNγ) is produced by replacing at least one residue which is located between residues 121 and 127 from a C-terminal of an epitope of a human interferon gamma (hIFNγ) SEQ ID NO: 39 via homologous substitution; and evaluating the efficacy of the isolated recombinant human interferon gamma (rhIFNγ) according to an expression level of a phosphorylation of signal transducers and activators of transcription 1 (p-STAT1) generated by the PBMC.

2. The method as claimed in claim 1, wherein homologous substitution consists of SEQ ID NO: 1.

3. The method as claimed in claim 2, wherein the isolated recombinant human interferon gamma (rhIFNγ) further includes a pharmaceutically acceptable excipient or a pharmaceutically acceptable carrier.

4. The method as claimed in claim 2, wherein the isolated recombinant human interferon gamma (rhIFNγ) up-regulates the expression level of the p-STAT1.

5. A method for evaluating an efficacy of an isolated recombinant human interferon gamma (rhIFNγ) for regulating a peripheral blood mononuclear cell (PBMC), comprising the steps of: providing the PBMC from a subject with anti-interferon gamma autoantibodies; mixing the isolated recombinant human interferon gamma (rhIFNγ) with the PBMC, wherein the isolated recombinant human interferon gamma (rhIFNγ) is produced by replacing residues which is located between residues 121 and 127 from a C-terminal of an epitope of a human interferon gamma (hIFNγ) of SEQ ID NO: 39 via homologous substitution of SEQ ID NO: 1; and evaluating the efficacy of the isolated recombinant human interferon gamma (rhIFNγ) according to an expression level of a phosphorylation of signal transducers and activators of transcription 1 (p-STAT1) generated by the PBMC.

* * * * *